(12) United States Patent
Kanayama et al.

(10) Patent No.: US 10,342,514 B2
(45) Date of Patent: Jul. 9, 2019

(54) ULTRASONIC DIAGNOSTIC APPARATUS AND METHOD OF ULTRASONIC IMAGING

(71) Applicant: Toshiba Medical Systems Corporation, Otawara-shi (JP)

(72) Inventors: Yuko Kanayama, Nasushiobara (JP); Akihiro Kakee, Nasushiobara (JP); Tetsuya Kawagishi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 2 days.

(21) Appl. No.: 14/318,878

(22) Filed: Jun. 30, 2014

(65) Prior Publication Data

US 2015/0005633 A1 Jan. 1, 2015

(30) Foreign Application Priority Data

Jul. 1, 2013 (JP) .................................. 2013-138111

(51) Int. Cl.
*A61B 8/00* (2006.01)
*A61B 8/08* (2006.01)

(52) U.S. Cl.
CPC .............. *A61B 8/485* (2013.01); *A61B 8/463* (2013.01); *A61B 8/5207* (2013.01); *A61B 8/488* (2013.01); *A61B 8/5223* (2013.01)

(58) Field of Classification Search
CPC ....... A61B 8/485; A61B 8/463; A61B 8/5223; A61B 8/5207
See application file for complete search history.

(56) References Cited

U.S. PATENT DOCUMENTS 6,371,912 B1    4/2002  Nightingale et al.
8,118,744 B2 *  2/2012  Palmeri .................... A61B 8/08
                                                        600/437

(Continued)

FOREIGN PATENT DOCUMENTS

CN     102667522 A     9/2012
JP     2009-531101 A   9/2009

(Continued)

OTHER PUBLICATIONS

Pengfei Song et al. "Comb-push Ultrasound Shear Elastography (CUSE): A Novel Method for Two-dimensional Shear Elasticity Imaging of Soft Tissues", IEEE Medical Imaging, 2011, 12 pages.

(Continued)

*Primary Examiner* — Angela M Hoffa
*Assistant Examiner* — Vani Gupta
(74) *Attorney, Agent, or Firm* — Oblon, McClelland, Maier & Neustadt, L.L.P.

(57) ABSTRACT

An ultrasonic diagnostic apparatus according to an embodiment includes a setting unit, a transmitter, a signal processing unit, and an image generating unit. The setting unit sets a plurality of ROIs within a scanning region. The transmitter transmits an ultrasonic wave for displacement generation on a plurality of transmission conditions corresponding to the respective ROIs from an ultrasonic probe and transmits an ultrasonic wave for observation that observes a displacement generated by each transmission of the ultrasonic wave for displacement generation, from the ultrasonic probe a plurality of times. The signal processing unit analyzes a plurality of pieces of reflected wave data, acquires a plurality of pieces of displacement information, and calculates distribution information on the respective transmission conditions. The image generating unit generates a plurality of pieces of image data based on the pieces of distribution information (Continued)

and composite image data by composing the pieces of image data.

11 Claims, 23 Drawing Sheets

(56) References Cited

U.S. PATENT DOCUMENTS

| | | | |
|---|---|---|---|
| 8,758,248 B2* | 6/2014 | Lin | G01S 7/52022 |
| | | | 600/438 |
| 9,332,962 B2* | 5/2016 | Kim | A61B 8/485 |
| 2005/0215899 A1 | 9/2005 | Trahey et al. | |
| 2009/0203997 A1* | 8/2009 | Ustuner | A61B 8/08 |
| | | | 600/443 |
| 2010/0069751 A1* | 3/2010 | Hazard | A61B 5/415 |
| | | | 600/438 |
| 2011/0184287 A1 | 7/2011 | McAleavey | |
| 2011/0245675 A1* | 10/2011 | Yoshida | A61B 8/461 |
| | | | 600/443 |
| 2012/0065507 A1* | 3/2012 | Brunke | A61B 8/12 |
| | | | 600/442 |
| 2012/0134233 A1 | 5/2012 | Lin et al. | |
| 2012/0158323 A1 | 6/2012 | Hazard et al. | |
| 2012/0253194 A1* | 10/2012 | Tamura | A61B 8/485 |
| | | | 600/438 |
| 2014/0276046 A1* | 9/2014 | Kim | A61B 8/485 |
| | | | 600/438 |

FOREIGN PATENT DOCUMENTS

| | | |
|---|---|---|
| JP | 2012-100997 | 5/2012 |
| JP | 2012-161562 | 8/2012 |

OTHER PUBLICATIONS

Mickael Tanter et al. "Quantitative Assessment of Breast Lesion Viscoelasticity: Initial Clinical Results Using Supersonic Shear Imaging", Ultrasound in Medicine and Biology, vol. 34, 2008, 14 pages.
Combined Office Action and Search Report dated Jan. 8, 2016 in Chinese Patent Application No. 201410306590.0 with English translation of category of cited documents.
Chinese Office Action dated Aug. 3, 2016 in Chinese Application No. 201410306590.0 (no English translation), 7 pages.
Office Action dated Apr. 11, 2017 in Japanese Patent Application No. 2013-138111.

* cited by examiner

| TRANS-MISSION CONDITION NUMBER | VISUALIZA-TION UPPER LIMIT DEPTH | VISUALIZA-TION LOWER LIMIT DEPTH | APER-TURE WIDTH | FOCUS DEPTH | DRIVE VOLTAGE | FRE-QUENCY | BURST LENGTH |
|---|---|---|---|---|---|---|---|
| 1 | x1 | y1 | a1 | d1 | . | . | . |
| 2 | x2 | y2 | a2 | d2 | . | . | . |
| . | . | . | . | . | . | . | . |
| . | . | . | . | . | . | . | . |
| . | . | . | . | . | . | . | . |

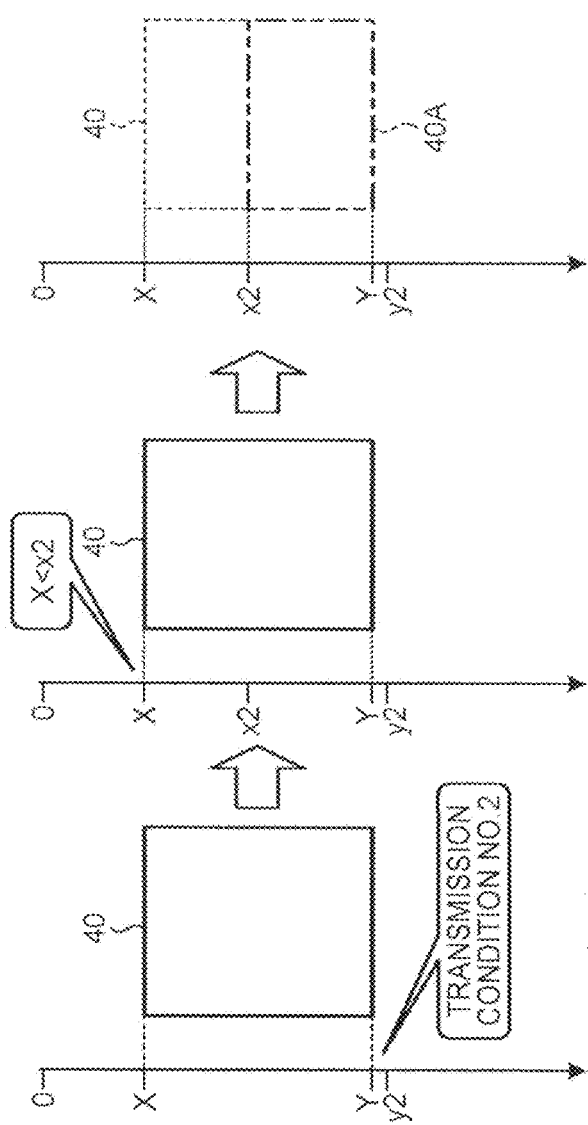

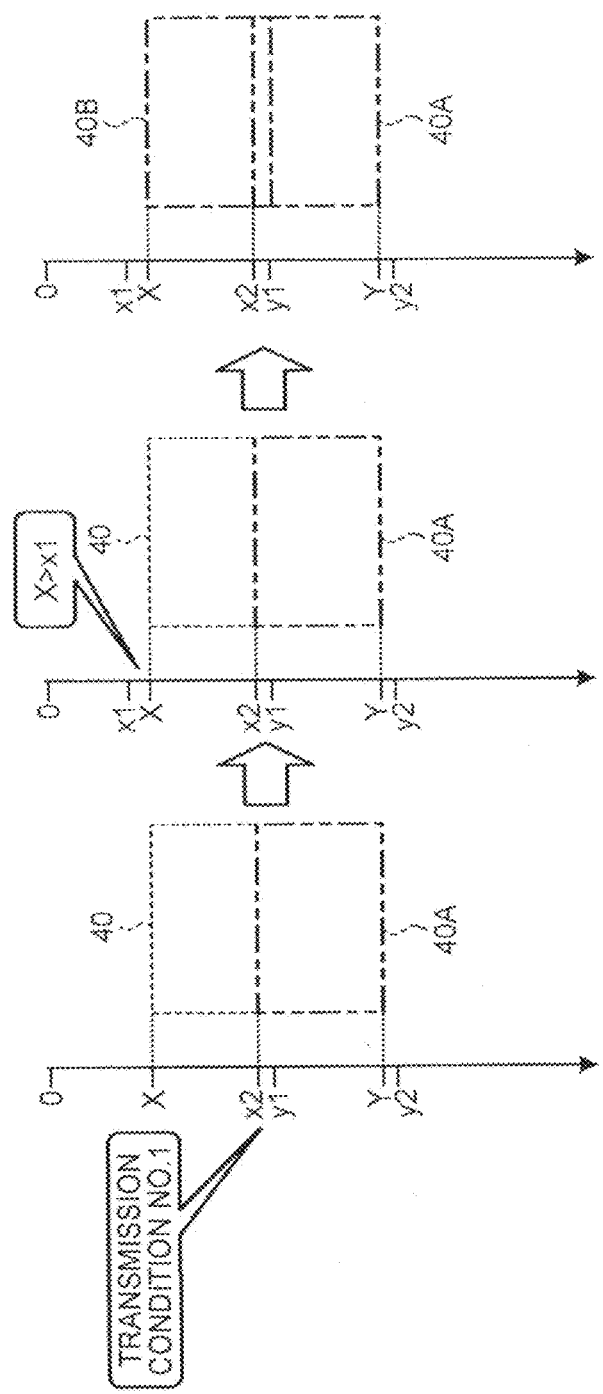

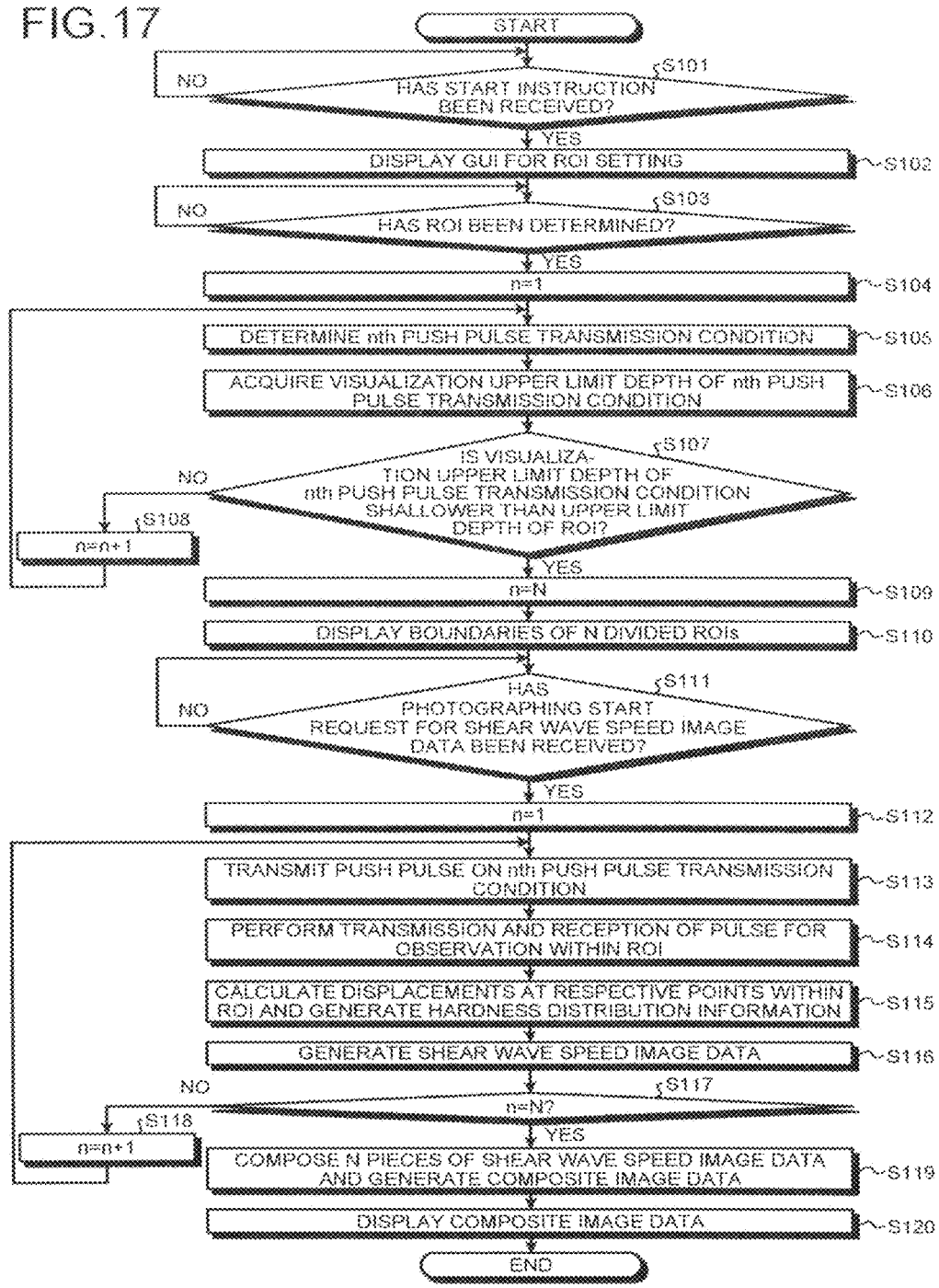

| WIDTH (WD) OF ROI IN DEPTH DIRECTION | NUMBER OF DIVISION |
|---|---|
| WD ≤ WD1 | 1 |
| WD1 < WD ≤ WD2 | 2 |
| WD2 < WD ≤ WD3 | 3 |
| WD3 < WD ≤ WD4 | 4 |
| . | . |
| . | . |

ULTRASONIC DIAGNOSTIC APPARATUS AND METHOD OF ULTRASONIC IMAGING

CROSS-REFERENCE TO RELATED APPLICATION

This application is based upon and claims the benefit of priority from Japanese Patent Application No. 2013-138111, filed on Jul. 1, 2013; the entire contents of which are incorporated herein by reference.

FIELD

Embodiments described herein relate generally to an ultrasonic diagnostic apparatus and a method of ultrasonic imaging.

BACKGROUND

Elastography is conventionally known that measures the hardness of living tissue and visualizes the distribution of the measured hardness. Elastography is utilized for diagnosing diseases in which the hardness of living tissue changes in accordance with the degree of progress of lesions such as hepatocirrhosis. In elastography, methods for evaluating hardness by displacing living tissue are broadly divided into the following two.

The first method is a method that visualizes relative hardness from the magnitude of distortion at points within a scanning section that is observed when living tissue is pressed and released from the surface of the body with an ultrasonic probe. The second method is a method that gives acoustic radiation force or mechanical vibrations to living tissue from the surface of the body, generates displacements by a shear wave, and observes displacements at points within a scanning section over time, thereby determining the propagation speed of the shear wave and determining a modulus of elasticity. In the first method, the local magnitude of distortion depends on the magnitude of manual movement of the ultrasonic probe, and it is evaluated whether a region of interest is softer or harder than the surroundings. In contrast, the second method can determine the absolute modulus of elasticity of a region of interest.

When a displacement is generated in living tissue by giving acoustic radiation force in the second method, however, depending on the beam shape of a burst wave (push pulse) for displacement generation, a displacement distribution suitable for the observation of the shear wave cannot be given especially in a shallow part. Specifically, living tissue over a wide area displaces by the push pulse, and displacement propagation in a lateral direction cannot be captured with high precision. This causes artifacts in a hardness image indicating the hardness of the living tissue.

BRIEF DESCRIPTION OF THE DRAWINGS

FIG. 11A and FIG. 11B are diagrams for illustrating an example of the processing of the setting unit according to the first embodiment;

FIG. 17 is a flowchart for illustrating a processing example of the ultrasonic diagnostic apparatus according to the first embodiment;

DETAILED DESCRIPTION

An ultrasonic diagnostic apparatus according to an embodiment includes a setting unit, a transmitter, a signal processing unit, and an image generating unit. The setting unit is configured to set a plurality of regions of interest comprising a first region of interest and a second region of interest that is adjacent to the first region of interest in a depth direction or that partly overlaps with the first region of interest in the depth direction within a given scanning region. The transmitter is configured to transmit an ultrasonic wave for displacement generation that causes a displacement in living tissue based on acoustic radiation force from an ultrasonic probe on a plurality of transmission conditions comprising at least a first transmission condition corresponding to the first region of interest and a second transmission condition corresponding to the second region of interest and to transmit an ultrasonic wave for observation that observes a displacement in living tissue within the scanning region, the displacement being generated along with each transmission of the ultrasonic wave for displacement generation, from the ultrasonic probe a plurality of times. The signal processing unit is configured to analyze a plurality of pieces of reflected wave data corresponding to the respective ultrasonic waves for observation transmitted from the ultrasonic probe, to acquire a plurality of pieces of displacement information corresponding to the scanning region, and to calculate distribution information based on the pieces of acquired displacement information on the respective transmission conditions. The image generating unit is configured to, based on the pieces of distribution information corresponding to the respective transmission conditions, generate a plurality of pieces of image data corresponding to the respective transmission conditions, and generate composite image data obtained by composing the pieces of image data.

The following describes embodiments of an ultrasonic diagnostic apparatus in detail with reference to the attached drawings.

First Embodiment

Figure 1:
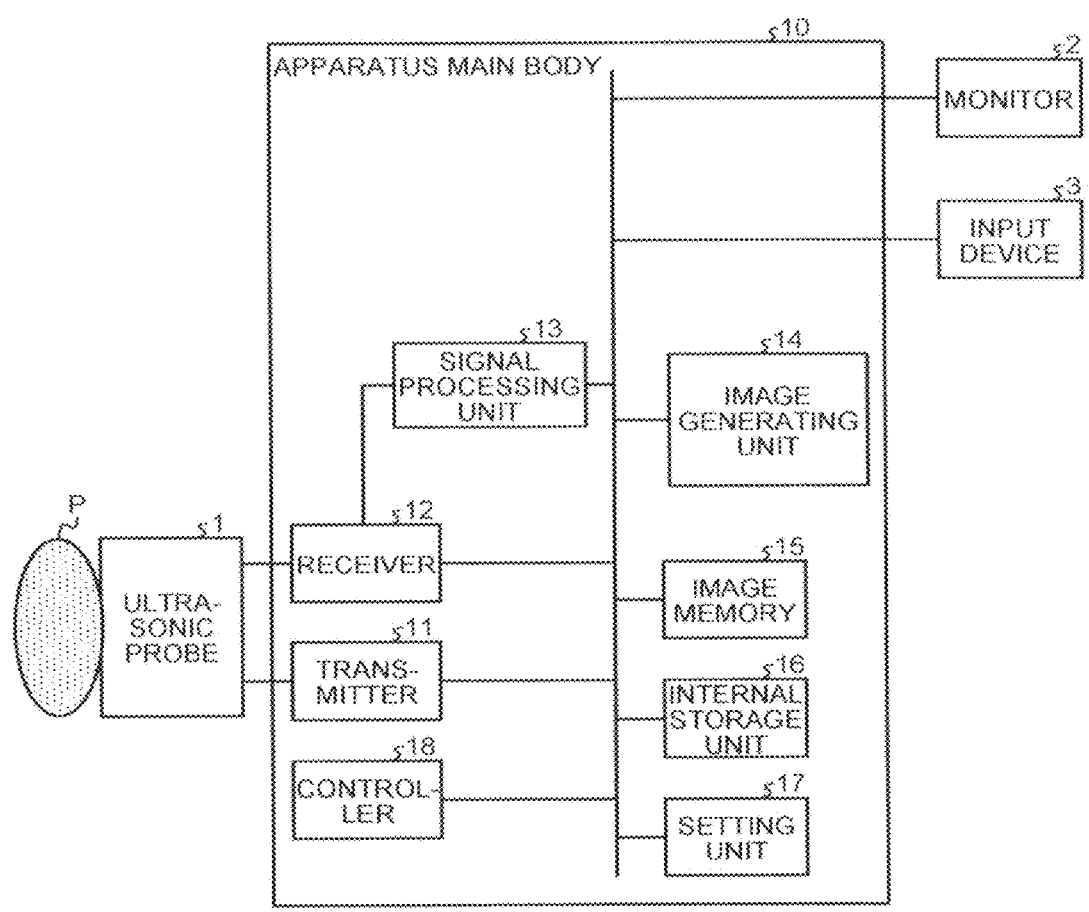
FIG. 1 is a block diagram illustrating a configuration example of an ultrasonic diagnostic apparatus according to a first embodiment.

Described first is the configuration of an ultrasonic diagnostic apparatus according to a first embodiment. FIG. 1 is a block diagram illustrating a configuration example of the ultrasonic diagnostic apparatus according to the first embodiment. As illustrated in FIG. 1, the ultrasonic diagnostic apparatus according to the first embodiment includes an ultrasonic probe 1, a monitor 2, an input device 3, and an apparatus main body 10.

The ultrasonic probe 1 has a plurality of transducer elements (piezoelectric transducer elements, for example), and these transducer elements generate ultrasonic waves based on drive signals supplied from a transmitter 11 of the apparatus main body 10 described below. The transducer elements of the ultrasonic probe 1 receive reflected waves from a subject P and convert them into electric signals. The ultrasonic probe 1 further includes a matching layer provided on the transducer elements and a backing member for preventing the ultrasonic waves from propagating backward from the transducer elements.

When the ultrasonic probe 1 transmits ultrasonic waves to the subject P, the transmitted ultrasonic waves are successively reflected by discontinuous surfaces in acoustic impedance in the body tissue of the subject P and are received as reflected waves by a plurality of elements of the ultrasonic probe 1. The elements receiving the reflected waves convert the reflected waves into reflected wave signals as electric signals. The amplitudes of the reflected wave signals generated by the respective transducer elements depend on differences in acoustic impedance on the discontinuous surfaces by which the ultrasonic wave is reflected. The reflected wave signal generated when a transmitted ultrasonic pulse is reflected by a moving bloodstream or a surface such as a heart wall is subjected to frequency shift by the Doppler effect depending on the velocity component of a moving body with respect to the ultrasonic transmission direction.

The first embodiment can be applied regardless of which of the following the ultrasonic probe 1 illustrated in FIG. 1 is: a one-dimensional ultrasonic probe in which a plurality of piezoelectric transducer elements are arranged in a row; a one-dimensional ultrasonic probe in which a plurality of piezoelectric transducer elements arranged in a row are mechanically oscillated; and a two-dimensional ultrasonic probe in which a plurality of piezoelectric transducer elements are arranged in a two-dimensional lattice manner.

The input device 3 includes a mouse, a keyboard, a button, a panel switch, a touch command screen, a foot switch, a trackball, or a joystick, receives various setting requests from an operator of the ultrasonic diagnostic apparatus, and transfers the received various setting requests to the apparatus main body 10.

The monitor 2 displays a graphical user interface (GUI) used by the operator of the ultrasonic diagnostic apparatus for inputting the various setting requests through the input device 3 or displays ultrasonic image data or the like generated in the apparatus main body 10.

The apparatus main body 10 is an apparatus that generates ultrasonic image data based on the reflected wave signal received by the ultrasonic probe 1 and includes, as illustrated in FIG. 1, the transmitter 11, a receiver 12, a signal processing unit 13, an image generating unit 14, an image memory 15, an internal storage unit 16, a setting unit 17, and a controller 18.

The transmitter 11 controls transmission directivity in ultrasonic transmission. Specifically, the transmitter 11 includes a rate pulse generator, a transmission delay unit, and a transmission pulser and supplies drive signals to the ultrasonic probe 1. The rate pulse generator repeatedly generates rate pulses for forming a transmission ultrasonic wave at a given pulse repetition frequency. The rate pulses pass through the transmission delay unit, thereby applying voltages to the transmission pulser with different transmission delay times. In other words, the transmission delay unit gives transmission delay times for the respective transducer elements, which are required for focusing the ultrasonic waves generated from the ultrasonic probe 1 in a beam form and determining transmission directivity, to the respective rate pulses generated by the rate pulse generator. The transmission pulser applies drive signals (drive pulses) to the ultrasonic probe 1 with timing based on the rate pulses. Transmission directions or the transmission delay times are stored in the internal storage unit 16 described below. The transmitter 11 refers to the internal storage unit 16 to control the transmission directivity.

The drive pulses propagate from the transmission pulser through a cable to the transducer elements within the ultrasonic probe 1 and are converted from electric signals to mechanical vibrations in the transducer elements. The mechanical vibrations are transmitted through the inside of a living body as ultrasonic waves. The ultrasonic waves having different transmission delay times for the respective transducer elements are focused to propagate in a certain direction. The transmission delay unit changes the transmission delay times to be given to the respective rate pulses, thereby desirably adjusting the transmission direction from a transducer element surface. The transmitter 11 controls the number and the positions (transmission aperture) of the transducer elements to be used in transmitting an ultrasonic beam and the transmission delay times in relation to the positions of the respective transducer elements constituting the transmission aperture, thereby giving the transmission directivity. A transmission delay circuit of the transmitter 11, for example, gives transmission delay times to the respective rate pulses generated by a pulser circuit, thereby controlling the position of a focus point in the depth direction of ultrasonic transmission (transmission focus).

The transmitter 11 has a function that enables instantly changing a transmission frequency, a transmission drive voltage, or the like in order to perform a given scan sequence based on instructions by the controller 18 described below. In particular, changes of the transmission drive voltage can be performed by a liner amplifier type oscillator circuit that can instantly switch the value or by a mechanism that electrically switches a plurality of power supply units.

The reflected waves of the ultrasonic waves transmitted by the ultrasonic probe 1 reach the transducer elements within the ultrasonic probe 1, are converted from mechanical vibrations to an electric signal (reflected wave signal) in the transducer elements, and are input to the receiver 12.

The receiver 12 controls reception directivity in ultrasonic reception. Specifically, the receiver 12 includes a pre-amplifier, an analog/digital (A/D) converter, a reception delay unit, and an adder and performs various processing on the reflected wave signals received by the ultrasonic probe 1 to generate reflected wave data. The pre-amplifier amplifies the reflected wave signals for respective channels to perform gain correction processing. The A/D converter performs A/D conversion on the reflected wave signals subjected to the gain correction. The reception delay unit gives reception delay times necessary for determining the reception directivity to the respective channels. The adder adds up the reflected wave signals (digital signals) having the reception delay times given thereto to generate the reflected wave data. The addition processing by the adder enhances a reflected component from a direction corresponding to the reception directivity of the reflected wave signals. Reception directions or the reception delay times are stored in the internal storage unit 16 described below. The receiver 12 refers to the internal storage unit 16 to control the reception directivity. The receiver 12 according to the first embodiment can also perform parallel simultaneous reception.

The signal processing unit 13 performs various kinds of signal processing on the reflected wave data generated from the reflected wave signals by the receiver 12. The signal processing unit 13 performs logarithmic amplification, envelope detection processing, or the like on the reflected wave data received from the receiver 12, thereby generating data (B mode data), in which signal intensity at each sample point is represented by brightness.

The signal processing unit 13 generates data (Doppler data) in which motion information based on the Doppler effect of a moving body is extracted at respective sample points within a scanning region from the reflected wave data received from the receiver 12. Specifically, the signal processing unit 13 generates the Doppler data in which an average velocity, a variance, a power value, or the like is extracted at respective sample points as the motion information of the moving body. Examples of the moving body include bloodstreams, tissue such as heart walls, and contrast media.

The ultrasonic diagnostic apparatus according to the first embodiment is an apparatus capable of measuring the hardness of living tissue and performing elastography that visualizes the distribution of the measured hardness. Specifically, the ultrasonic diagnostic apparatus according to the first embodiment applies acoustic radiation force and generates displacements in living tissue, thereby performing elastography.

In other words, the transmitter 11 according to the first embodiment transmits an ultrasonic wave for displacement generation that causes a displacement in living tissue based on acoustic radiation force. The transmitter 11, for example, transmits the ultrasonic wave for displacement generation (push pulse) that causes a displacement, which then results in a shear wave, by the acoustic radiation force from the ultrasonic probe 1. The transmitter 11 according to the first embodiment transmits an ultrasonic wave for observation that observes a displacement in living tissue within the scanning region, the displacement being generated along with each transmission of the ultrasonic wave for displacement generation, from the ultrasonic probe 1 a plurality of times. The transmitter 11, for example, transmits the ultrasonic wave for observation (pulse for observation) that observes a displacement generated by the ultrasonic wave for displacement generation (push pulse) from the ultrasonic probe 1 a plurality of times at each of the scanning lines within the scanning range. The pulse for observation is transmitted in order to observe the propagation speed of the shear wave generated by the push pulse at respective sample points within the scanning range. The pulse for observation is generally transmitted at each scanning line within the scanning range a plurality of times (100 times, for example). The receiver 12 generates the reflected wave data from the reflected wave signals of the pulse for observation transmitted by the respective scanning lines within the scanning range.

The signal processing unit 13 analyzes a plurality of pieces of reflected wave data corresponding to the respective ultrasonic waves for observation (a plurality of pulses for observation) transmitted from the ultrasonic probe 1, acquires a plurality of pieces of displacement information corresponding to the scanning region, and calculates distribution information based on the pieces of acquired displacement information. Specifically, the signal processing unit 13 analyzes the reflected wave data of the pulse for observation transmitted a plurality of times at each scanning line within the scanning region and calculates hardness distribution information indicating the hardness distribution of the scanning region as distribution information. More specifically, the signal processing unit 13 measures the propagation speed of the shear wave generated by the push pulse at the respective sample points, thereby generating the hardness distribution information of the scanning region.

The signal processing unit 13, for example, calculates correlation of the reflected wave data of the pulse for observation. The signal processing unit 13 thus generates motion information (tissue Doppler data) over a plurality of time phases at a plurality of respective sample points of each scanning line. The signal processing unit 13 integrates the velocity components of the tissue Doppler data over the time phases obtained at the respective sample points of each scanning line with respect to time. The signal processing unit 13 thereby calculates the displacements of the respective sample points of each scanning line over the time phases. The signal processing unit 13 then determines times when the displacements are maximized at the respective sample points. The signal processing unit 13 acquires the times when the maximum displacements are obtained as arrival times of shear waves at the respective sample points. The signal processing unit 13 then spatially differentiates the arrival times of the shear waves at the respective sample points, thereby calculating the propagation speeds of the shear waves at the respective sample points. Hereinafter, the "propagation speed of a shear wave" will be referred to as a "shear wave speed".

The signal processing unit 13 encodes the shear wave propagation speeds by color and performs mapping onto corresponding sample points, thereby generating the hardness distribution information. Harder tissue gives a larger shear wave speed, whereas softer tissue gives a smaller shear wave speed. In other words, the value of the shear wave speed is a value indicating the hardness (the modulus of elasticity) of tissue. In the above case, the pulse for observation is a transmission pulse for tissue Doppler. The shear wave speed may be calculated by the signal processing unit 13 by detecting it based on the cross correlation of displacements of tissue on adjacent scanning lines, not based on the times when the displacements are maximized at the respective sample points.

The signal processing unit 13 may calculate a Young's modulus or a shear modulus of elasticity from the shear wave speed and generate the hardness distribution information as distribution information from the calculated Young's modulus or shear modulus of elasticity. Any of the shear wave speed, the Young's modulus, and the shear modulus of elasticity can be used as a physical quantity representing the hardness of living tissue. The following describes a case when the signal processing unit 13 uses the shear wave speed as the physical quantity representing the hardness of tissue. In all the embodiments described below, displacement information may be used as the distribution information in addition to the shear wave speed and the Young's modulus and the shear modulus of elasticity that are calculated based on the shear wave speed.

A shear wave generated by one time of push pulse transmission attenuates along with propagation. When attempting to observe the shear wave speed over a wide range, a shear wave generated by a push pulse transmitted by one specific scanning line attenuates along with propagation and becomes unobservable when being sufficiently far from the push pulse position.

In such a case, the push pulse is required to be transmitted at a plurality of positions in the lateral direction. Specifically, the scanning region (or a region of interest) is divided into a plurality of regions in the lateral direction. The transmitter 11, before transmitting and receiving the pulse for observation at the respective divided regions, transmits the push pulse at different scanning line positions to generate a shear wave. In this case, the lateral position of the push pulse transmission is generally set near each region. Such shift of the lateral position of transmission is, for example, performed with the transmitter 11 referring to a table that previously sets a distance from the left end of a region to be changed. When the number of simultaneous parallel reception is limited to a small number, the transmitter 11 transmits a push pulse once to the respective regions divided in the lateral direction and then repeats the processing that transmits the pulse for observation at each scanning line a plurality of times, thereby performing the transmission and reception of an ultrasonic wave for displacement observation in all the respective regions.

The image generating unit 14 generates ultrasonic image data from the data generated by the signal processing unit 13. The image generating unit 14 generates B mode image data representing the intensity of the reflected wave with brightness from B mode data generated by the signal processing unit 13. The image generating unit 14 generates Doppler image data representing moving body information from the Doppler data generated by the signal processing unit 13. The Doppler image data is velocity image data, variance image data, power image data, or image data obtained by combining these.

The image generating unit 14 generates image data based on the distribution information generated by the signal processing unit 13. Specifically, the image generating unit 14 generates hardness image data, in which the hardness of tissue is displayed in colors, from the hardness distribution information generated by the signal processing unit 13. The image generating unit 14, for example, generates shear wave speed image data as the hardness image data.

Typically, the image generating unit 14 scan-converts a scanning line signal sequence of ultrasonic scanning into a scanning line signal sequence of a video format represented by the one for television or the like to generate ultrasonic image data for display. Specifically, the image generating unit 14 performs coordinate transformation in accordance with a scanning manner of ultrasonic waves by the ultrasonic probe 1 to generate the ultrasonic image data for display. The image generating unit 14 performs, other than the scan conversion, various kinds of image processing such as image processing (smoothing processing) that regenerates a brightness average image using a plurality of frames after the scan conversion, and image processing (edge enhancing processing) using a differential filter within an image. The image generating unit 14 combines supplemental information (character information of various parameters, scales, body marks, or the like) with the ultrasonic image data.

In other words, the B mode data, the Doppler data, and the distribution information are ultrasonic image data before the scan conversion processing, whereas the data generated by the image generating unit 14 is ultrasonic image data for display after the scan conversion processing. When the signal processing unit 13 generates three-dimensional data (three-dimensional B mode data, three-dimensional Doppler data, and three-dimensional distribution information), the image generating unit 14 performs coordinate transformation in accordance with a scanning manner of ultrasonic waves by the ultrasonic probe 1 to generate volume data. The image generating unit 14 performs various kinds of rendering processing on the volume data to generate two-dimensional image data for display.

The image memory 15 is a memory that stores therein the image data for display generated by the image generating unit 14. The image memory 15 can also store therein the data generated by the signal processing unit 13. The B mode data, the Doppler data, and the distribution information stored in the image memory 15 can be, for example, called up by an operator after a diagnosis and become ultrasonic image data for display through the image generating unit 14.

The internal storage unit 16 stores therein control programs for performing image processing and display processing, diagnostic information (patient IDs and doctors' opinions, for example), and various kinds of data such as diagnostic protocols and various kinds of body marks. The internal storage unit 16 is also used for storing the image data stored in the image memory 15 as needed. The data stored in the internal storage unit 16 can be transferred to external devices through an interface unit (not illustrated).

The setting unit 17 sets ultrasonic transmission conditions for the transmitter 11. Specifically, the setting unit 17 sets transmission conditions of the push pulse the transmitter 11 transmits from the ultrasonic probe 1. Processing performed by the setting unit 17 according to the first embodiment is described below in detail.

The controller 18 controls the entire processing of the ultrasonic diagnostic apparatus. Specifically, the controller 18 controls the processing of the transmitter 11, the receiver 12, the signal processing unit 13, the image generating unit 14, and the setting unit 17 based on various kinds of setting requests input from the operator through the input device 3 and various kinds of control programs and various kinds of data read from the internal storage unit 16. The controller 18 performs control so as to display the ultrasonic image data for display stored in the image memory 15 on the monitor 2.

The transmitter 11, the receiver 12, and the like incorporated into the apparatus main body 10 may be configured by hardware such as integrated circuits or may be configured by programs modularized as software.

The entire constitution of the ultrasonic diagnostic apparatus according to the first embodiment has been described. With the constitution, the ultrasonic diagnostic apparatus according to the first embodiment performs push pulse transmission to visualize the hardness of living tissue.

In conventional technologies, push pulses are transmitted on one kind of transmission condition, and it has been difficult to obtain high-precision hardness image data over a wide area. FIG. 2 to FIG. 5 illustrate this situation. FIG. 2 to FIG. 5 are diagrams for illustrating conventional technologies.

Figure 2:
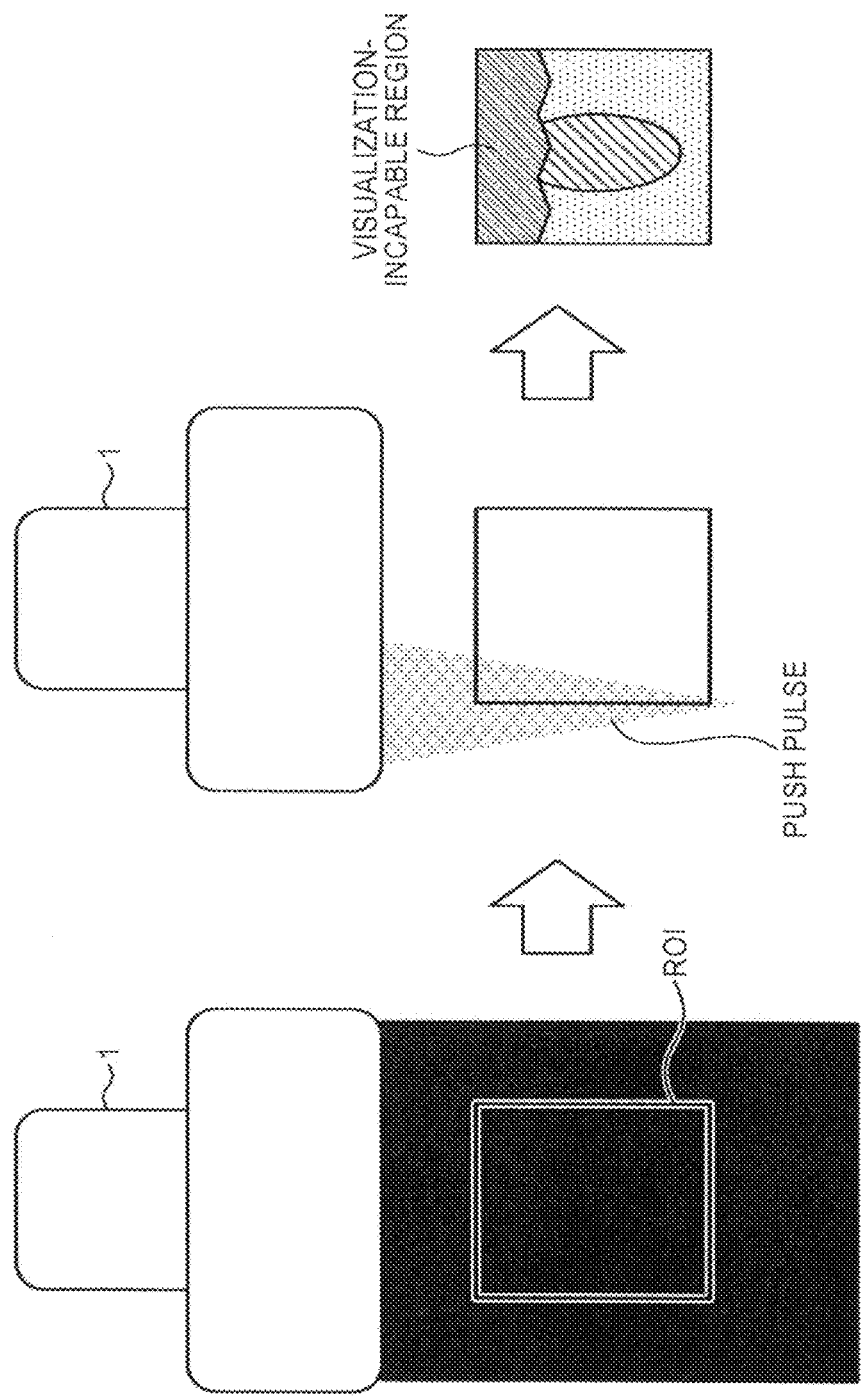
FIG. 2, FIG. 3, FIG. 4, and FIG. 5 are diagrams for illustrating a conventional technology.

When performing push pulse transmission for displacement generation in living tissue, in order to generate a sufficiently large displacement at a part having a certain degree of depth, a push pulse is required to be transmitted on a transmission condition focused on a deep part with a transmission aperture having a certain degree of size. The left diagram illustrated in FIG. 2 illustrates a region of interest (ROI) set to display hardness image data within the scanning range of the ultrasonic probe 1. The central diagram illustrated in FIG. 2 illustrates the manner how a push pulse focused on a deep part of the ROI is transmitted from a wide transmission aperture set by the ultrasonic probe 1.

Based on the transmission condition, although in the deep part it is easy to capture the manner how a shear wave propagates, whereas in a shallow part the expected manner of the propagation of the shear wave cannot be seen, and the shear wave speed cannot be determined accurately. The right diagram illustrated in FIG. 2 exemplifies shear wave speed image data generated as the hardness image data by the push pulse focused on the deep part of the ROI. As illustrated in the right diagram of FIG. 2, the shear wave speed image data generated by the push pulse focused on the deep part of the ROI involves a region (a visualization-incapable region) in which the shear wave speed cannot be visualized in a short-distance region (shallow part). Due to this visualization-incapable region, the shear wave speed image data illustrated in the right diagram of FIG. 2 is seen as an artifact.

Figure 3:
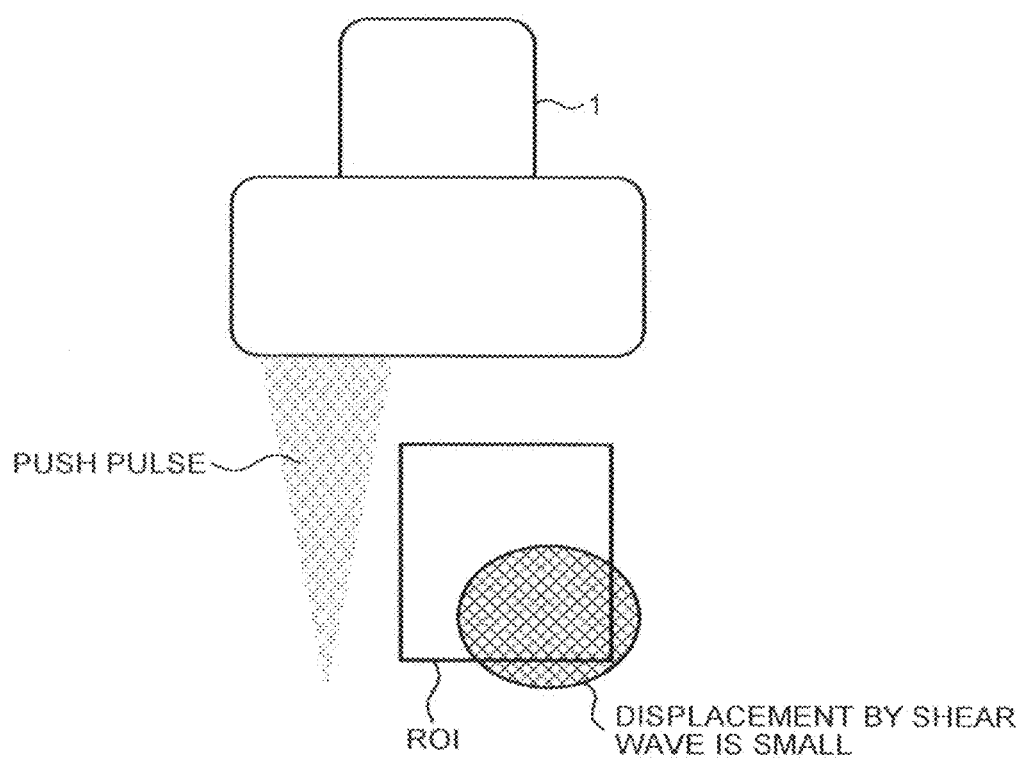
Figure 4:
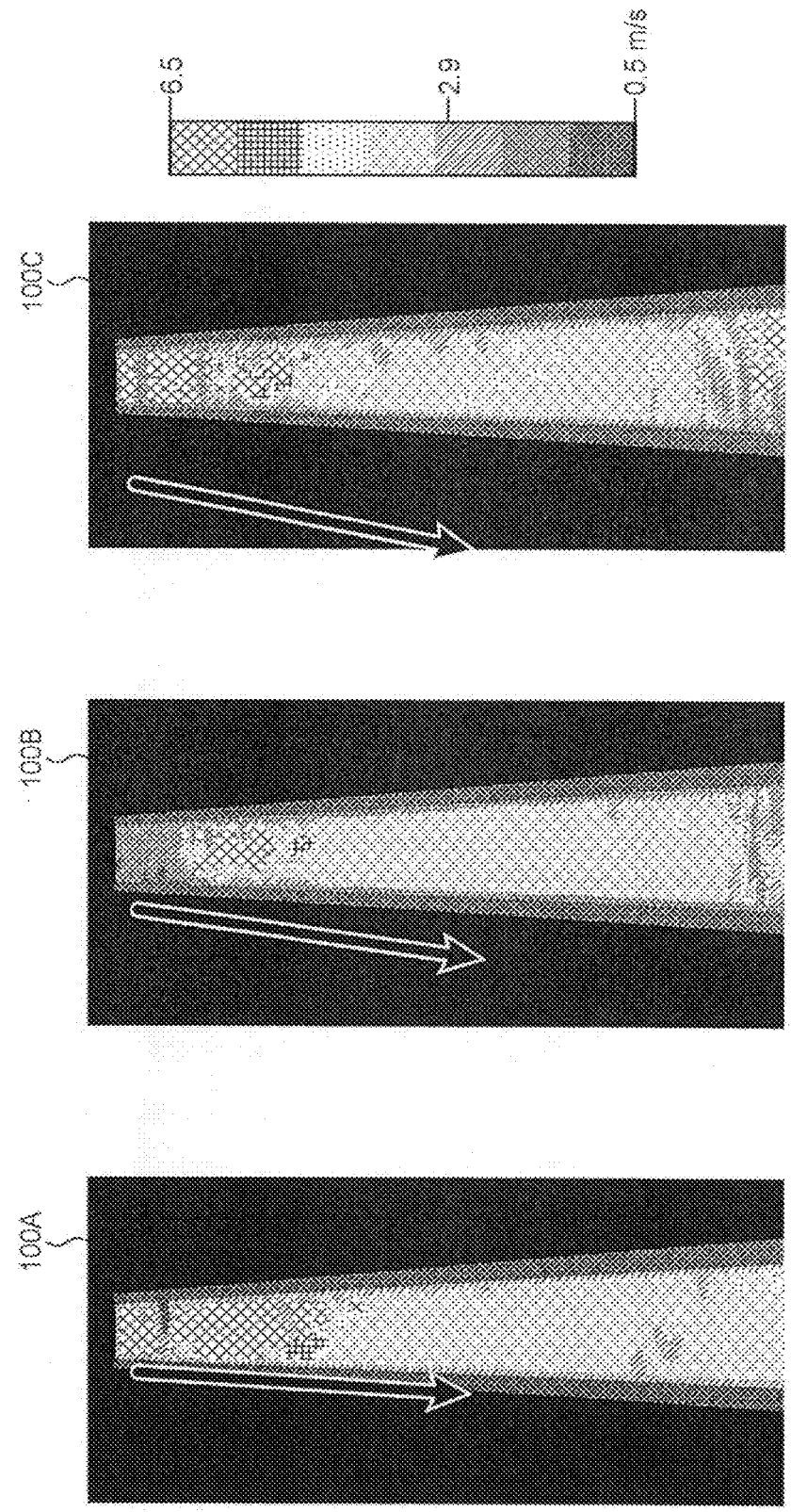

It is known that the visualization-incapable region in the short-distance region (shallow part) is attributable to the incapability of observing the propagation of the shear wave at a push pulse generation position. As illustrated in FIG. 3, locating the push pulse generation position away from the ROI is considered as a method to eliminate the visualization-incapable region in the short-distance region. An image data 100A illustrated in FIG. 4 is shear wave speed image data generated by transmitting a push pulse to the left end of the ROI. An image data 100B illustrated in FIG. 4 is shear wave speed image data generated by transmitting a push pulse at a position separated leftward from the left end of the ROI. An image data 100C illustrated in FIG. 4 is shear wave speed image data generated by transmitting a push pulse at a position separated further leftward from the left end of the ROI. However, in all the image data 100A, image data 100B, and image data 100C, artifacts in which the shear wave speed (units: m/s) is high occur in the shallow part.

Figure 5:
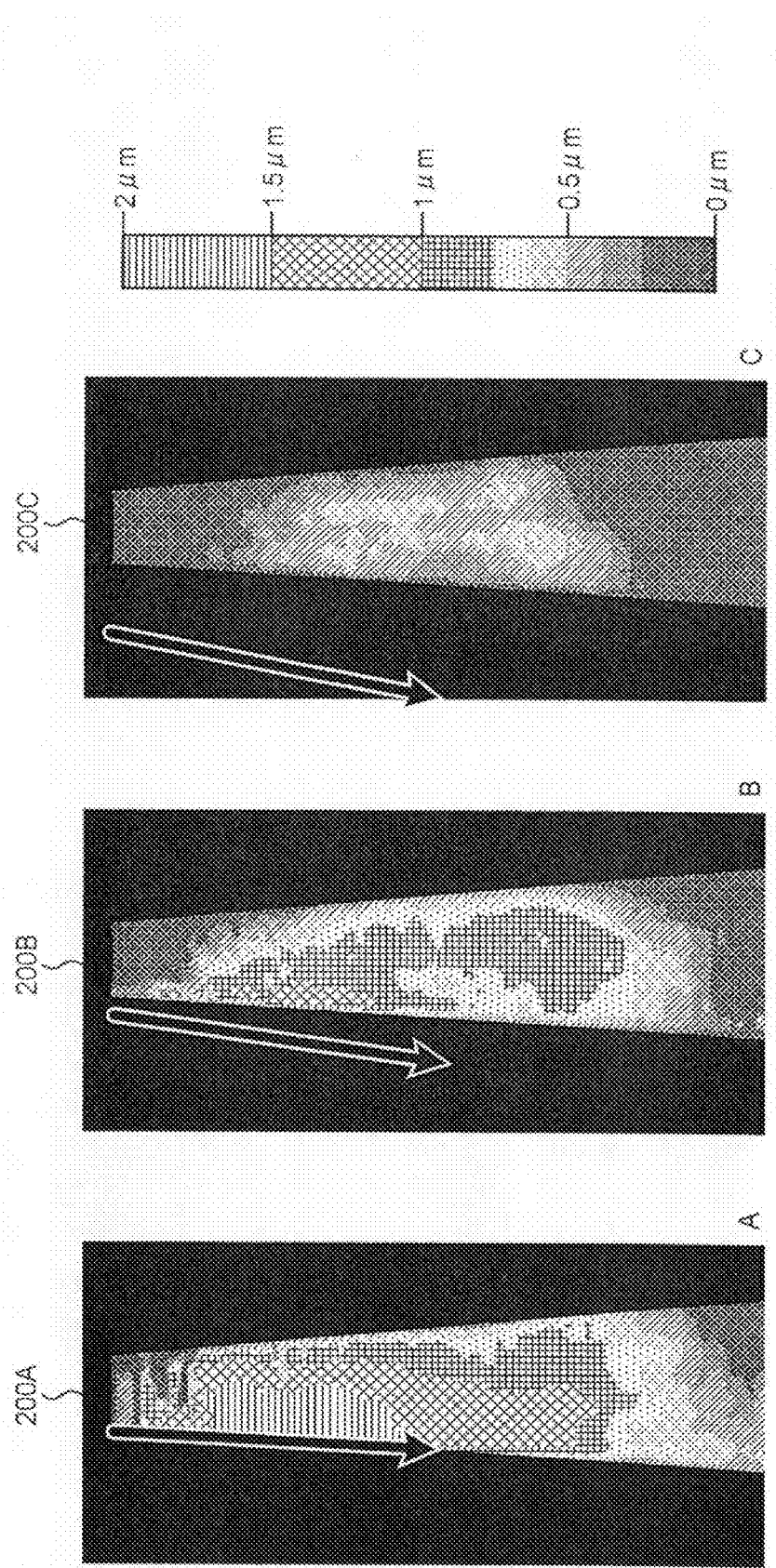

The possible reason why the shear wave speed in the shallow part cannot be determined with high precision is that ideal propagation of a shear wave does not occur because of a large width (aperture width) for generating an initial displacement in order to ensure observation sensitivity in the deep part. In addition, when the lateral position of the push pulse transmission is located away from the ROI, the generated shear wave attenuates before reaching the ROI, and a smaller displacement is generated in the deep part in particular. An image data 200A illustrated in FIG. 5 is maximum displacement image data visualizing the maximum displacements (units: μm) of the respective sample points calculated when generating the image data 100A. An image data 200B illustrated in FIG. 5 is maximum displacement image data visualizing the maximum displacements of the respective sample points calculated when generating the image data 100B. An image data 200C illustrated in FIG. 5 is maximum displacement image data visualizing the maximum displacements of the respective sample points calculated when generating the image data 100C. When comparing the image data 200A, the image data 200B, and the image data 200C, it is observed that the maximum displacement becomes smaller within the ROI (in the deep part of the ROI in particular) as the lateral position of the push pulse transmission becomes further away from the ROI.

When the lateral position of the push pulse transmission is located away from the ROI, therefore, as illustrated in FIG. 3, a region in which a smaller displacement is generated occurs in the deep part in particular. This results in the incapability of capturing a displacement in the deep part with high sensitivity, giving degraded penetration. As illustrated in FIG. 4, for example, in the image data 100B and the image data 100C, a region having a high shear wave speed, which is not seen in the image data 100A, additionally occurs in the deep part like an artifact. For living tissue in which movement occurs due to causes other than shear waves such as pulsation, it is required to generate an even a little bit larger displacement in order to acquire high-precision hardness image data.

In conventional technologies, however, because push pulses are transmitted on one kind of transmission condition, it is difficult to obtain high-precision hardness image data over a wide area. Owing to this, in the practical clinic sites, there are some cases in which even when an artifact occurs due to the characteristic of a push pulse, it cannot be determined whether information visualized in hardness image data is information properly reflecting the hardness of living tissue or information based on noise to be ignored. The present embodiment transmits a push pulse on a plurality of kinds of transmission conditions in order to obtain high-precision image data over a wide area.

Figure 6:
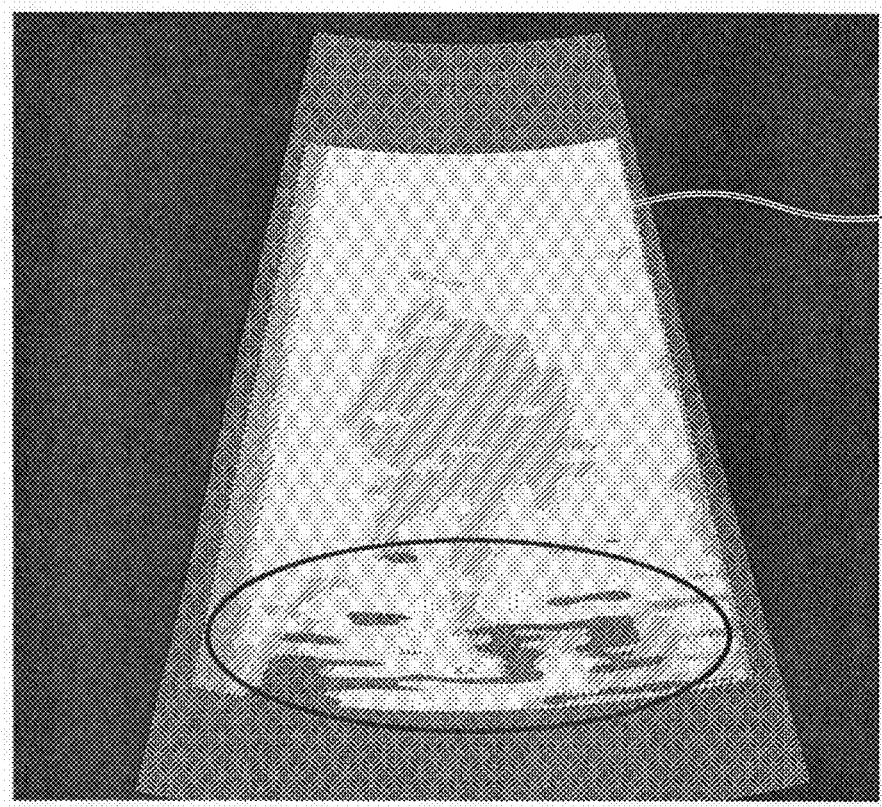
FIG. 6 and FIG. 7 are diagrams for illustrating the concept of the first embodiment.
Figure 7:
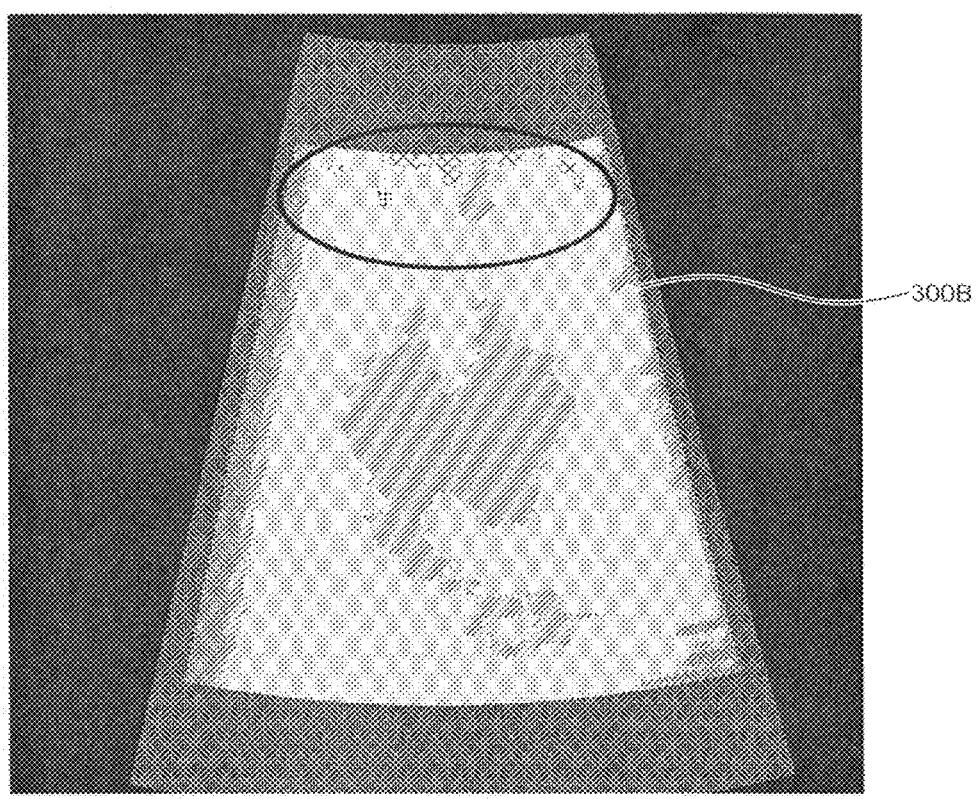

FIG. 6 and FIG. 7 are diagrams for illustrating the concept of the present embodiment. An image data 300A illustrated in FIG. 6 is, for example, shear wave speed image data generated when the focus of the push pulse is set at a short distance of 4 cm. An image data 300B illustrated in FIG. 7 is, for example, shear wave speed image data generated when the focus of the push pulse is set at a long distance of 8 cm. In the image data 300A focused on the short distance, a displacement is generated in the shallow part, and the shear wave speed is determined with high precision, imparting high image quality to the shallow part. In the image data 300A, however, no displacement is generated in the deep part, degrading image quality in the deep part (refer to the inside of the ellipse in FIG. 6). In contrast, in the image data 300B focused on the long distance, a displacement is generated in the deep part, and the shear wave speed is determined with high precision, imparting high image quality to the deep part. In the image data 300B, however, shear wave with a desirable shape is not generated in the shallow part, degrading image quality in the shallow part (refer to the inside of the ellipse in FIG. 7).

However, when combining the region in which the displacement is generated by the push pulse on the transmission condition in which the focus is set at the short distance of 4 cm and the region in which the displacement is generated by the push pulse on the transmission condition in which the focus is set at the long distance of 8 cm, the entire ROI can be completely covered. In other words, when combining the image data 300A and the image data 300B, high-quality shear wave speed image data can be generated over the entire ROI.

For this purpose, the setting unit 17 illustrated in FIG. 1 sets a plurality of regions of interest including a first region of interest and a second region of interest that is adjacent to the first region of interest in the depth direction or that partly overlaps with the first region of interest in the depth direction within a given scanning region. The transmitter 11 according to the first embodiment transmits the ultrasonic wave for displacement generation that causes a displacement in living tissue based on the acoustic radiation force from the ultrasonic probe 1 on a plurality of transmission conditions. In other words, the transmitter 11 transmits a plurality of ultrasonic waves for displacement generation (push pulses) that cause displacements, which then result in a shear wave, caused by the acoustic radiation force from the ultrasonic probe 1 on the respective transmission conditions independently. Specifically, the transmitter 11 transmits the ultrasonic wave for displacement generation from the ultrasonic probe on the transmission conditions including a first transmission condition corresponding to the first region of interest and a second transmission condition corresponding to the second region of interest. The transmitter 11 transmits the ultrasonic wave for observation that observes a displacement in living tissue within the scanning region, the displacement being generated along with each transmission of the ultrasonic wave for displacement generation, from the ultrasonic probe 1 a plurality of times. In other words, the transmitter 11 transmits the ultrasonic wave for observation (pulse for observation) that observes displacements generated by the respective ultrasonic waves for displacement generation by a plurality of respective scanning lines within the scanning region from the ultrasonic probe 1 a plurality of times.

The signal processing unit 13 calculates the distribution information (the hardness distribution information, for example) on the respective transmission conditions. Specifically, the signal processing unit 13 calculates at least first distribution information based on a plurality of pieces of displacement information corresponding to at least the first region of interest based on the ultrasonic wave for displacement generation transmitted on the first transmission condition and second distribution information based on a plurality of pieces of displacement information corresponding to at least the second region of interest based on the ultrasonic wave for displacement generation transmitted on the second transmission condition. The image generating unit 14 generates a plurality of pieces of image data (hardness image data, for example) corresponding to the respective transmission conditions using pieces of distribution information (hardness distribution information, for example) corresponding to the respective transmission conditions. The image generating unit 14 generates composite image data having the pieces of image data (the hardness image data, for example) composed therein. Specifically, the image generating unit 14 generates first image data based on the first distribution information, generates second image data based on the second distribution information, and generates the composite image data based on a composite result of at least the first image data and the second image data. The image generating unit 14, for example, generates the composite image data as the hardness image data of the scanning region.

The respective transmission conditions differ in at least one of the focus depth, the transmission aperture, the transmission frequency, and the burst length (wave number) of the push pulse. The transmission conditions are set by the setting unit 17. In other words, the setting unit 17 sets the transmission conditions so that a region obtained by combining regions in which the shear wave propagation speeds are observed in living tissue by a plurality of respective push pulses will completely cover the scanning region in which the shear wave speed is observed. In other words, the setting unit 17 sets the transmission conditions so that a visualization-incapable region of shear wave speed image data generated by a push pulse on one transmission condition will be a visualization-capable region of shear wave speed image data generated by a push pulse on another transmission condition.

Specifically, the setting unit 17 sets a plurality of divided regions as a plurality of regions of interest in a region of interest (ROI) set by an operator as the scanning region and sets transmission conditions of the push pulse on which the shear wave speeds are observed in substantially the entire living tissue of the respective regions of interest (respective divided regions). In other words, the setting unit 17 sets the push pulse transmission conditions on which the shear wave speed is observed in substantially the entire living tissue of the respective divided regions obtained by dividing the regions of interest, thereby setting the transmission conditions.

The setting unit 17, for example, divides the region of interest into a plurality of divided regions in the depth direction. The image generating unit 14 composes a plurality of pieces of image data (a plurality of pieces of hardness image data, for example) corresponding to the respective transmission conditions based on the divided regions (regions of interest) to generate the composite image data.

The internal storage unit 16 according to the first embodiment stores therein, for each of the transmission conditions, depth information that associates an upper limit depth and a lower limit depth in the depth direction in which a displacement substantial enough to calculate shear wave speed based on the shear waves generated by the ultrasonic wave for displacement generation transmitted on the transmission condition is generated. In other words, the internal storage unit 16 according to the first embodiment stores therein, for each of the transmission conditions, depth information that associates an upper limit depth and a lower limit depth in the depth direction with each other at which the shear wave speed is observed by the push pulse transmitted on the transmission condition. The setting unit 17 according to the first embodiment sets the transmission conditions based on the upper limit depth and the lower limit depth of the region of interest set by the operator and the depth information.

Figure 8:
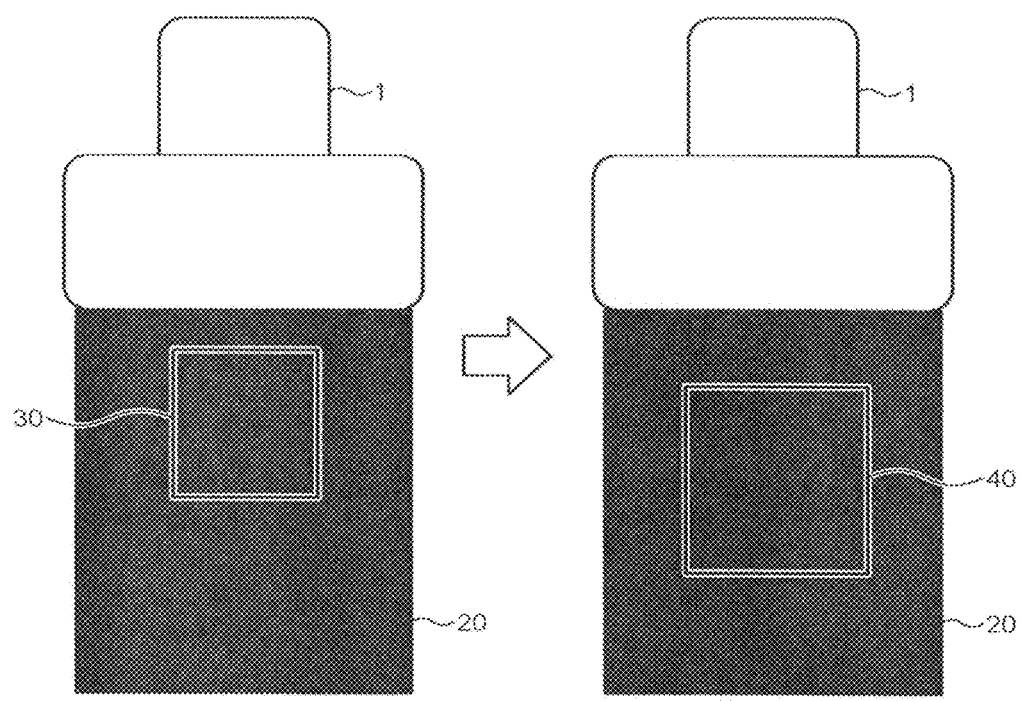
FIG. 8 is a diagram for illustrating an example of ROI setting.

The following describes processing performed by the setting unit 17 and the like according to the first embodiment with reference to the drawings. The divided regions are represented as "divided ROIs" below. FIG. 8 is a diagram for illustrating an example of ROI setting.

First, as illustrated in the left diagram of FIG. 8, the operator operates the ultrasonic probe 1 to perform B mode scan on a region including a region for which the hardness of living tissue is desired to be observed. This causes B mode image data 20 to be displayed, and the operator, for example, presses a button of the input device 3 to input a start instruction for starting the processing of the setting unit 17. As illustrated in the left diagram of FIG. 8, the controller 18 that has received the start instruction displays an initial ROI 130 indicating a region in which shear wave propagation is observed on the B mode image data 20 in a superimposed manner. The operator operates a mouse or the like of the input device 3 to change the position and size of the initial ROI 30 as needed. This causes the operator to determine an ROI 40 for observation as illustrated in the right diagram of FIG. 8.

Figures 9, 10:
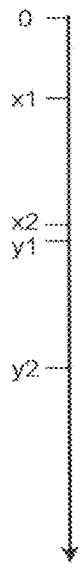
FIG. 9 and FIG. 10 are diagrams for illustrating the example of the depth information table.

The setting unit 17 divides the ROI 40 into the divided ROIs. In the first embodiment, the setting unit 17 refers to a depth information table stored in the internal storage unit 16 in advance and divides the ROI 40 into the divided ROIs in the depth direction. FIG. 9 and FIG. 10 are diagrams illustrating an example of the depth information table.

As exemplified in FIG. 9, the internal storage unit 16 according to the first embodiment stores therein depth information that associates "visualization upper limit depth" and "visualization lower limit depth" as the depth information and "aperture width", "focus depth", "drive voltage", "frequency", and "burst length" as the transmission conditions with each other under each "transmission condition number". These pieces of information are, for example, acquired in advance by a preliminary test using a phantom or the like and are stored in the internal storage unit 16.

"Transmission condition No. 1" exemplified in FIG. 9 indicates that, when using a push pulse transmitted on the transmission condition of "aperture width: a1, focus depth: d1", and the like, the upper limit depth (visualization upper limit depth) at which the shear wave speed is observed with high precision is "x1", whereas the lower limit depth (visualization lower limit depth) at which the shear wave speed is observed with high precision is "y1". "Transmission condition No. 2" exemplified in FIG. 9 indicates that, when using a push pulse transmitted on the transmission condition of "aperture width: a2, focus depth: d2", and the like, the visualization upper limit depth is "x2", whereas the visualization lower limit depth is "y2".

Ranges in the depth direction set by the visualization upper limit depths and the visualization lower limit depths under the respective transmission condition numbers are set so that they will overlap with each other. As illustrated in FIG. 10, for example, "x1 to y1" and "x2 to y2" share the range of "x2 to y1" in the depth direction.

The internal storage unit 16 may store therein the lateral position of the push pulse transmission as the transmission condition for each piece of depth information. The internal storage unit 16 may store therein, for example, a transmission condition in which a position separated from one end of the region of interest by a lateral distance of "J1" is set as the lateral position of the push pulse transmission for the depth information of "x1, y1", while a transmission condition in which a position separated from one end of the region of interest by a distance of "J2 (J2<J1)" is set as the lateral position of the push pulse transmission for the depth information of "x2, y2".

FIG. 11A and FIG. 11B are diagrams illustrating an example of processing of the setting unit according to the first embodiment. As illustrated in the left diagram of FIG. 11A, first, the setting unit 17 acquires the lower limit depth "Y" of the ROI 40 and the upper limit depth "X" of the ROI 40. The setting unit 17 then determines the push pulse transmission condition that can observe a shear wave at the lower limit depth "Y" of the ROI 40 by referring to the "visualization lower limit depth" exemplified in FIG. 9. In other words, the setting unit 17 searches for the "visualization lower limit depth" that is deeper than "Y" and has the minimum difference from "Y". In the left diagram of FIG. 11A, the setting unit 17 searches for "lower limit depth: y2". This causes the setting unit 17, as illustrated in the left diagram of FIG. 11A, to determine the transmission condition of "transmission condition No. 2" to be a "first push pulse transmission condition".

The setting unit 17 determines whether the "first push pulse transmission condition", that is, the visualization upper limit depth "x2" of "transmission condition No. 2" is shallower than the upper limit depth "X" of the ROI 40. In the central diagram of FIG. 11A, because "X<x2", the setting unit 17 determines that the visualization-incapable region occurs within the ROI 40 on the "first push pulse transmission condition" and then proceeds to the determination processing of a "second push pulse transmission condition". As illustrated in the right diagram of FIG. 11A, because "X<x2", the setting unit 17 sets a divided ROI 40A of "x2 to Y" within the ROI 40.

As illustrated in the left diagram of FIG. 11B, the setting unit 17 determines the push pulse transmission condition that can observe a shear wave at the upper limit depth "x2" of the ROI 40A by referring to the "visualization lower limit depth" exemplified in FIG. 9. In other words, the setting unit 17 searches for the "visualization lower limit depth" that is deeper than "x2" and has the minimum difference from "x2". In the left diagram of FIG. 11B, the setting unit 17 searches for "lower limit depth: y1". This causes the setting unit 17, as illustrated in the left diagram of FIG. 11B, to determine the transmission condition of "transmission condition No. 1" to be the "second push pulse transmission condition".

The setting unit 17 determines whether the "second push pulse transmission condition", that is, the visualization upper limit depth "x1" of "transmission condition No. 1" is shallower than the upper limit depth "X" of the ROI 40. In the central diagram of FIG. 11B, because "X>x1", the setting unit 17 determines that the visualization-incapable region occurring on the "first push pulse transmission condition" can be visualized on the "second push pulse transmission condition". As illustrated in the right diagram of FIG. 11B, because "X>x1", the setting unit 17 sets a divided ROI 40B of "X to y1" within the ROT 40. The setting unit 17 has set a plurality of divided ROIs that completely cover the ROI 40 and then ends the transmission condition setting processing. Thus, the setting unit 17 repeats the transmission condition determination processing until the visualization upper limit depth of the "nth push pulse transmission condition" becomes shallower than the upper limit depth "X" of the ROI 40.

Figure 12A:
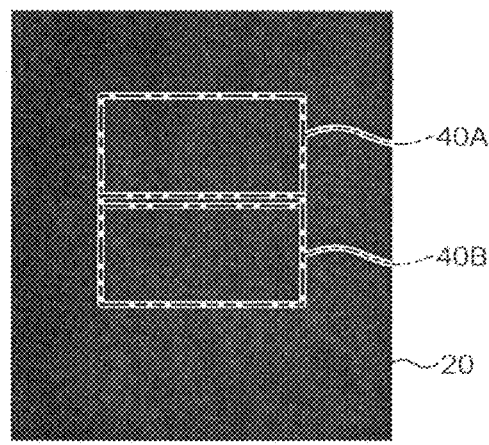
FIG. 12A, FIG. 12B, and FIG. 12C are diagrams for illustrating the display control by the controller according to the first embodiment.
Figure 12B:
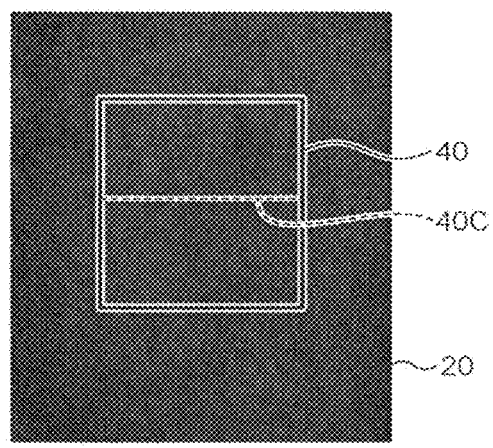
Figure 12C:
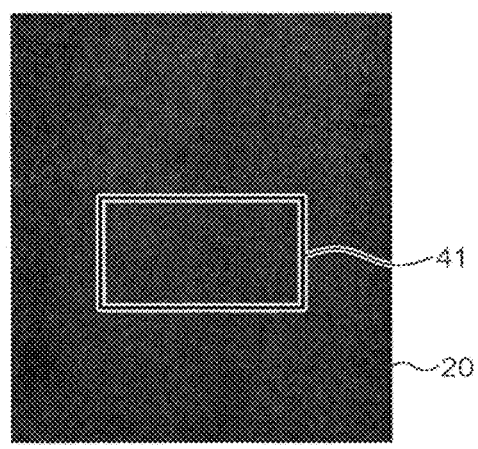

The controller 18 causes the monitor 2 to display the regions of interest set by the setting unit 17, that is, the divided ROIs divided by the setting unit 17. FIG. 12A, FIG. 12B, and FIG. 12C are diagrams for illustrating display control by the controller according to the first embodiment.

The monitor 2, for example, as illustrated in FIG. 12A, displays the divided ROI 40A and the divided ROI 40B on the B mode image data 20 in a superimposed manner by the control of the controller 18. Alternatively, the monitor 2, as illustrated in FIG. 12B, displays a boundary line 40C of the divided ROI 40A and the divided ROI 40B together with the ROI 40 on the B mode image data 20 in a superimposed manner. The boundary line 40C is, for example, set at a position of "(x2+y1)/2".

By referring to a screen illustrated in FIG. 12A or FIG. 12B, the operator can check in advance how many kinds of independent push pulse transmission are required over the entire ROI 40 set by the operator in order to obtain high-precision shear wave speed image data. In the above example, due to the ROI 40 divided into two, the operator will confirm that two kinds of independent push pulse transmission are required. FIG. 12C is referred to below.

Figure 13:
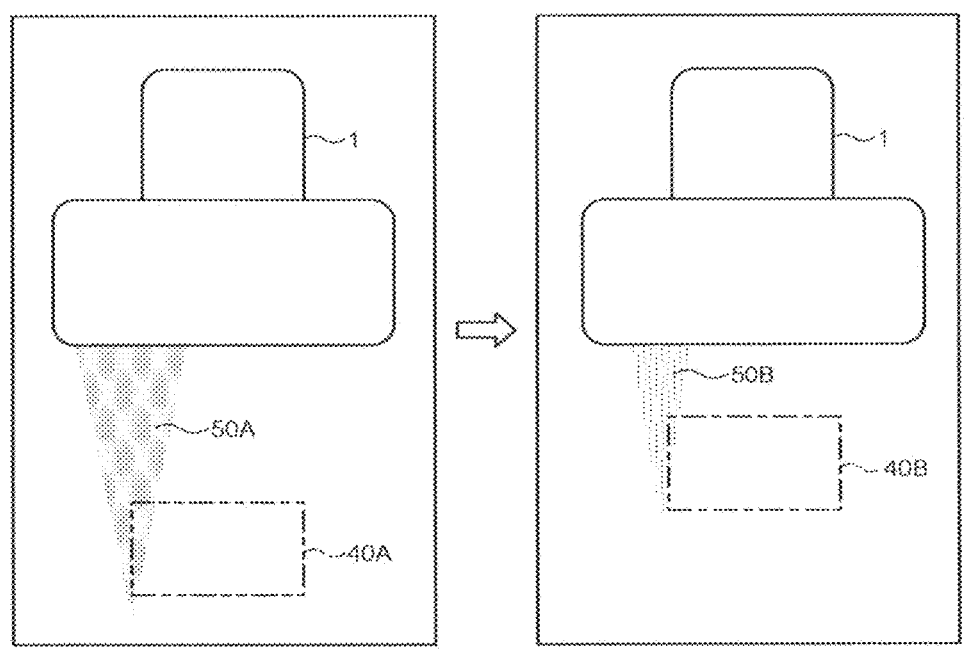
FIG. 13 is a diagram for illustrating a transmitter according to the first embodiment.

When the operator checks the above screen, approves the setting of the setting unit 17, and inputs an imaging start request for shear wave speed image data, the following processing is started by the control of the controller 18. FIG. 13 is a diagram for illustrating the transmitter according to the first embodiment.

In the above example, as illustrated in the left diagram of FIG. 13, the transmitter 11 first transmits a push pulse 50A on the "first push pulse transmission condition". As illustrated in the left diagram of FIG. 13, the push pulse 50A is a push pulse focused on within the range of the divided ROI 40A in the depth direction by a large transmission aperture width. By the control of the transmitter 11 and the receiver 12, the ultrasonic probe 1 performs the transmission and reception of a pulse for observation within the ROI 40.

As illustrated in the right diagram of FIG. 13, the transmitter 11 transmits a push pulse 50B on the "second push pulse transmission condition". As illustrated in the right diagram of FIG. 13, the push pulse 50B is a push pulse focused on within the range of the divided ROI 40B in the depth direction by a small transmission aperture width. By the control of the transmitter 11 and the receiver 12, the ultrasonic probe 1 performs the transmission and reception of a pulse for observation within the ROI 40.

When comparing the left diagram and the right diagram of FIG. 13, the lateral position of the push pulse transmission 50B is positioned apart from the lateral position of the push pulse transmission 50A. The example illustrated in FIG. 13 indicates that the transmitter 11 adjusts the lateral position of the push pulse transmission 50A using the distance "J2" corresponding to "transmission condition No. 2" and adjusts the lateral position of the push pulse transmission 50B using the distance "J1" corresponding to "transmission condition No. 1". The left diagram of FIG. 13 exemplifies an example of J2 being "0".

The transmitter 11 sets the number of transmission lateral positions of the push pulse 50A and the push pulse 50B using a shear wave propagation distance within typical living tissue and the width of the ROI 40 in the lateral direction. When the number of lateral position of the push pulse transmission 50A and the push pulse transmission 50B is plural, the transmitter 11 sets a range in the lateral direction within which the pulse for observation is transmitted by push pulse transmission at one place. When the number of transmission positions of the push pulse 50A and the push pulse 50B is plural, the transmitter 11 may change the range in the lateral direction within which the pulse for observation is transmitted by push pulse transmission at one place. These pieces of setting information are, for example, stored in advance in the internal storage unit 16.

The signal processing unit 13 generates the hardness distribution information on the ROI 40 for the "first push pulse transmission condition" and generates the hardness distribution information on the ROI 40 for the "second push pulse transmission condition". FIG. 14, FIG. 15A, FIG. 15B, FIG. 15C, and FIG. 16 are diagrams for illustrating the image generating unit according to the first embodiment.

Figure 14:
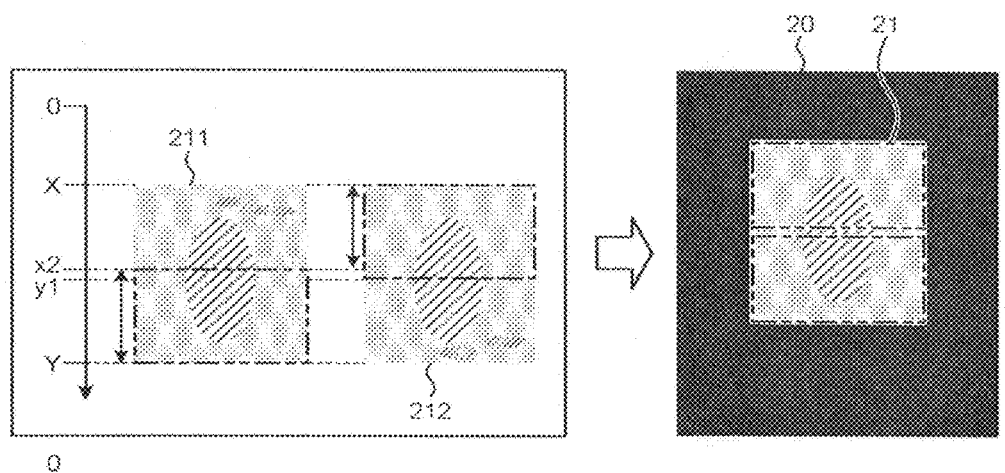
FIG. 14, FIG. 15A, FIG. 15B, FIG. 15C, and FIG. 16 are diagrams for illustrating the image generating unit according to the first embodiment.

The image generating unit 14, for example, as illustrated in the left diagram of FIG. 14, generates shear wave speed data 211 on the "first push pulse transmission condition" and shear wave speed image data 212 on the "second push pulse transmission condition". The image generating unit 14, for example, as illustrated in the left diagram of FIG. 14, cuts the range of "x2 to Y" out of the shear wave speed image data 211 and cuts the range of "X to x2" out of the shear wave speed image data 212. The image generating unit 14 then composes the two pieces of cut-out image data. This causes the image generating unit 14, as illustrated in the right diagram of FIG. 14, to generate shear wave speed image data 21. The shear wave speed image data 21 is hardness image data in which high-precision shear wave propagation speeds are mapped over the entire ROI 40.

In the right diagram of FIG. 14, the shear wave speed image data 21 is superimposed on the B mode image data 20, and in addition, the dotted frame lines indicating the ranges of the divided ROI 40A and the divided ROI 40B is superimposed thereon.

Figure 15A:
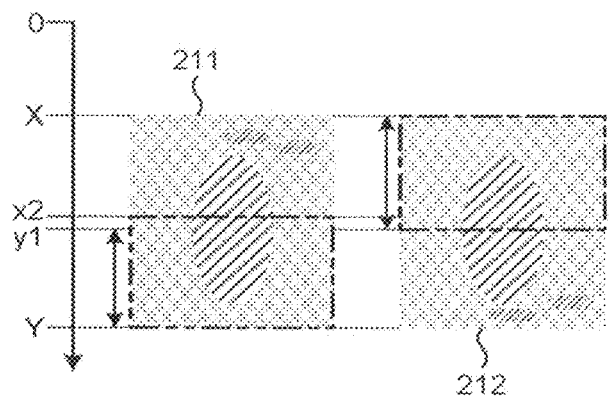
Figure 15B:
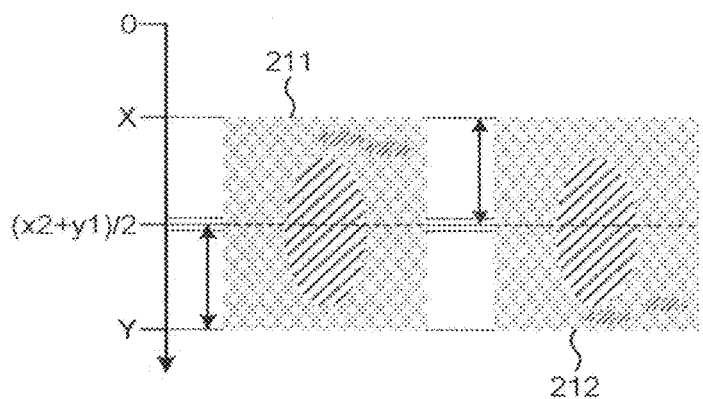

The image composition processing performed by the image generating unit 14 is not limited to the processing exemplified in FIG. 14. The image generating unit 14, for example, as illustrated in FIG. 15A, may cut the range of "y1 to Y" out of the shear wave speed image data 211, cut the range of "X to y1" out of the shear wave speed image data 212, and compose the two pieces of cut-out image data to generate the shear wave speed image data 21. Alternatively, the image generating unit 14, for example, as illustrated in FIG. 15B, may cut the range of "(x2+y1)/2 to Y" out of the shear wave speed image data 211, cut the range of "X to (x2+y1)/2" out of the shear wave speed image data 212, and compose the two pieces of cut-out image data to generate the shear wave speed image data 21.

Figure 15C:
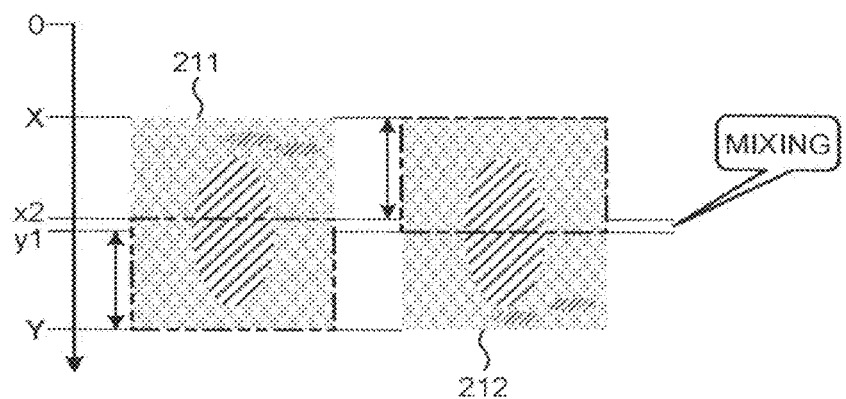

Alternatively, the image generating unit 14, for example, as illustrated in FIG. 15C, cuts the range of "y1 to Y" out of the shear wave speed image data 211 and cuts the range of "X to x2" out of the shear wave speed image data 212. The image generating unit 14, for example, as illustrated in FIG. 15C, mixes the range of "x2 to y1" of the shear wave speed image data 211 and the range of "x2 to y1" of the shear wave speed image data 212 by weighed addition using coefficients set linearly in the depth direction or averaging. The image generating unit 14 may combine these three pieces of image data, thereby generating the shear wave speed image data 21. The image composition processing exemplified in FIG. 15C can prevent the boundary between the divided ROIs from being seen as an artifact.

Figure 16:
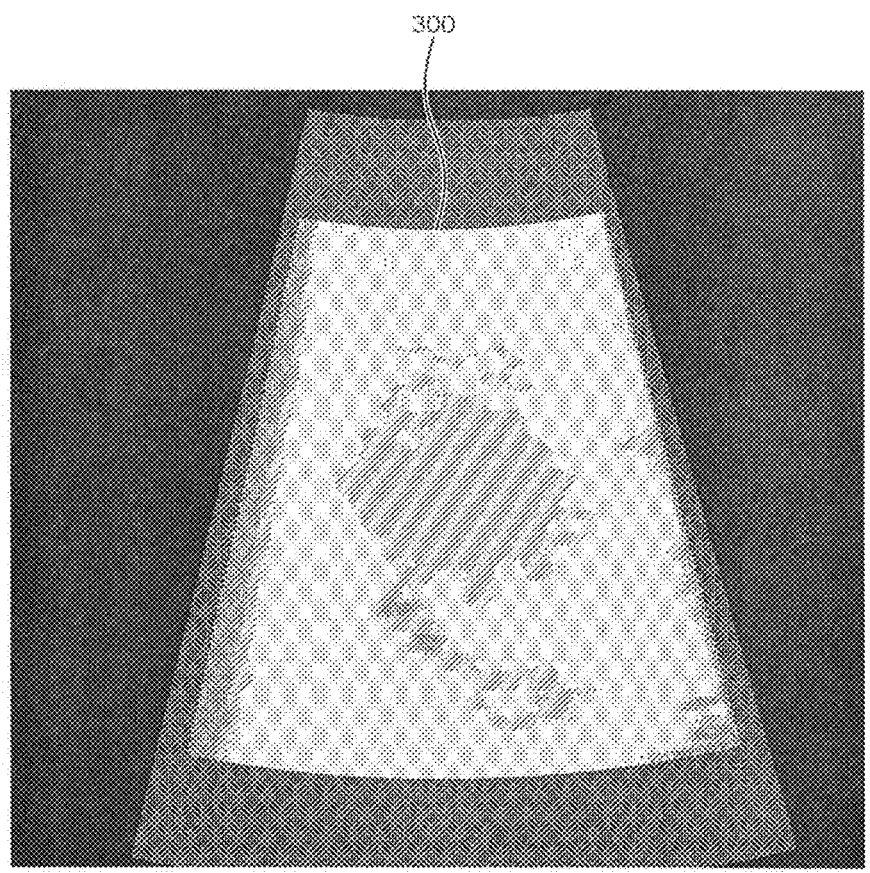

An image data 300 illustrated in FIG. 16 indicates shear wave speed image data obtained by combining the upper part of the image data 300A illustrated in FIG. 6 and the lower part of the image data 300B illustrated in FIG. 7 by the image generating unit 14 based on the two divided ROIs set by the setting unit 17. The image data 300 is hardness image data in which high-precision shear wave propagation speeds are mapped, after the artifact of the image data 300A and the artifact of the image data 300B are removed.

The present embodiment may, for example, generate image data obtained by averaging and composing the shear wave speed image data 211 and the shear wave speed image data 212 as the shear wave speed image data 21. This can also generate the shear wave speed image data 21 with the artifact of the shear wave speed image data 211 and the artifact of the shear wave speed image data 212 reduced by the averaging processing.

The present embodiment may generate the hardness distribution information and the hardness image data for each divided ROI limitedly and may compose pieces of hardness image data of the divided ROIs in accordance with the division manner of the ROIs.

Thus, the first embodiment allows the operator to obtain, even when the ROI 40 is a wide area, high-quality shear wave speed image data over its entire range without taking care of the size of the ROI 40 set by the operator. In the above example, the ROI 40 is divided into the two stages in accordance with the width of the ROI 40 in the depth direction, and the push pulse having a shallow focal distance and a narrow aperture width is applied to the shallow range to generate the shear wave speed image data 212. The push pulse having a deep focal length and a wide aperture width is applied to the deep range to generate the shear wave speed image data 211. Finally, the two pieces of shear wave speed image data are combined to be displayed.

The operator can check how many kinds of different push pulse transmission are required by referring to the screen exemplified in FIG. 12A or the screen exemplified in FIG. 12B. However, as is clear from the above generation processing of the shear wave speed image data, when the push pulse is transmitted on two kinds of transmission conditions, for example, the time required for generating one frame of shear wave speed image data is doubled compared with conventional ones. When the operator desires to keep a frame rate at a high level in accordance with inspection conditions, he/she can refer to the boundaries of the divided ROIs and readjust the ROI 40 so that division will not be performed. The operator, for example, as illustrated in FIG. 12C, readjusts the ROI 40 to an ROI 41 having a size small enough to fit inside the divided ROI 40B to generate high-quality shear wave speed image data with one kind of push pulse. In such a case, shear wave speed image data of the ROI 41 is generated and displayed on the "first push pulse transmission condition".

Described next with reference to FIG. 17 is an example of processing of the ultrasonic diagnostic apparatus according to the first embodiment. FIG. 17 is a flowchart for illustrating a processing example of the ultrasonic diagnostic apparatus according to the first embodiment.

As illustrated in FIG. 17, the controller 18 of the ultrasonic diagnostic apparatus according to the first embodiment determines whether a start instruction for stating the processing of the setting unit 17 has been received from the operator (Step S101). If the start instruction has not been received (No at Step S101), the controller 18 waits until the start instruction is received.

If the start instruction has been received (Yes at Step S101), the monitor 2 displays a GUI for ROI setting by the control of the controller 18 (Step S102, refer to FIG. 8). The controller 18 then determines whether the ROI has been determined (Step S103). If the ROI has not been determined (No at Step S103), the controller 18 waits until the ROI is set. If the ROI has been set (Yes at Step S103), the setting unit 17 sets "n=1" (Step S104), refers to the lower limit depth of the ROI and the depth information table, and determines the nth push pulse transmission condition (Step S105). The setting unit 17 acquires the visualization upper limit depth of the nth push pulse transmission condition (Step S106).

The setting unit 17 determines whether the visualization upper limit depth of the nth push pulse transmission condition is shallower than the upper limit depth of the ROI (Step S107). If the visualization upper limit depth of the nth push pulse transmission condition is deeper than the upper limit depth of the ROI (No at Step S107), the setting unit 17 increments "n" to "n=n+1" (Step S108), then returns to Step S105 to determine the nth push pulse transmission condition.

If the visualization upper limit depth of the nth push pulse transmission condition is shallower than the upper limit depth of the ROI (Yes at Step S107), the setting unit 17 sets "n=N" (Step S109), sets N transmission conditions, and notifies the controller 18 of the fact that the N divided ROIs have been set. The transmission conditions and the position information of the divided ROIs set by the setting unit 17 are, for example, stored in the internal storage unit 16 by the control of the controller 18.

By the control of the controller 18, the monitor 2 displays the boundaries of the N divided ROIs (Step S110). After Step S110, the operator may perform the readjustment of the ROI as exemplified in FIG. 12C. The following is described with the assumption that the N divided ROIs have been approved by the operator.

The controller 18 determines whether an imaging start request for shear wave speed image data has been received from the operator (Step S111). If the imaging start request has not been received (No at Step S111), the controller 18 waits until the imaging start request is received.

If the imaging start request has been received (Yes at Step S111), the controller 18 sets "n=1" (Step S112). By the control of the controller 18, the transmitter 11 acquires the nth push pulse transmission condition from the internal storage unit 16 and transmits the push pulse from the ultrasonic probe 1 on the nth push pulse transmission condition (Step S113).

By the control of the transmitter 11 and the receiver 12, the ultrasonic probe 1 performs the transmission and reception of the pulse for observation within the ROI (Step S114), and the signal processing unit 13 calculates displacements at respective points (respective sample points) within the ROI and generates the hardness distribution information (Step S115). The image generating unit 14 generates the shear wave speed image data on the nth push pulse transmission condition (Step S116). The controller 18 determines whether "n=N" (Step S117). If "n≠N" (No at Step S117), the controller 18 increments; "n" to "n=n+1" (Step S118), and the transmitter 11 returns to Step S113 to transmit the push pulse from the ultrasonic probe 1 on the nth push pulse transmission condition.

If "n=N" (Yes at Step S117), by the instruction of the controller 18, the image generating unit 14 composes N pieces of shear wave speed image data to generate composite image data (Step S119). By the control of the controller 18, the monitor 2 displays the composite image data as the shear wave speed image data of the entire ROI (Step S120). This ends the photographing processing for the shear wave speed image data.

When the request input by the operator is an imaging request for video of the shear wave speed image data, the pieces of processing from Step S112 to Step S120 are repeated by the control of the controller 18 until an imaging end request is received.

As described above, the first embodiment causes the internal storage unit 16 to store therein the depth information table that associates the visualization upper limit and the visualization lower limit with each other for each of the push pulse transmission conditions. The setting unit 17 sets a transmission condition that generates no visualization-incapable region in the respective regions obtained by dividing the ROI based on the width of the ROI in the depth direction set by the operator and the depth information, thereby setting a plurality of kinds of push pulse transmission conditions. In other words, in the first embodiment, the setting unit 17 uses the depth information table in order to give a push pulse that generates an ideal shear wave in accordance with the respective places within the ROI. This causes the image generating unit 14 to generate a plurality of pieces of hardness image data (shear wave speed image data in the above) corresponding to the respective push pulse transmission conditions and composes the generated pieces of hardness image data in accordance with the division pattern of the ROI. Such composite image data is hardness image data with artifacts substantially removed. Thus, the first embodiment can obtain high-quality images indicating the hardness of living tissue. The first embodiment, for example, can also reduce the chances of the operator wavering in his/her judgment about whether the obtained shear wave speed image data is a reliable image.

Second Embodiment

Figure 18A:
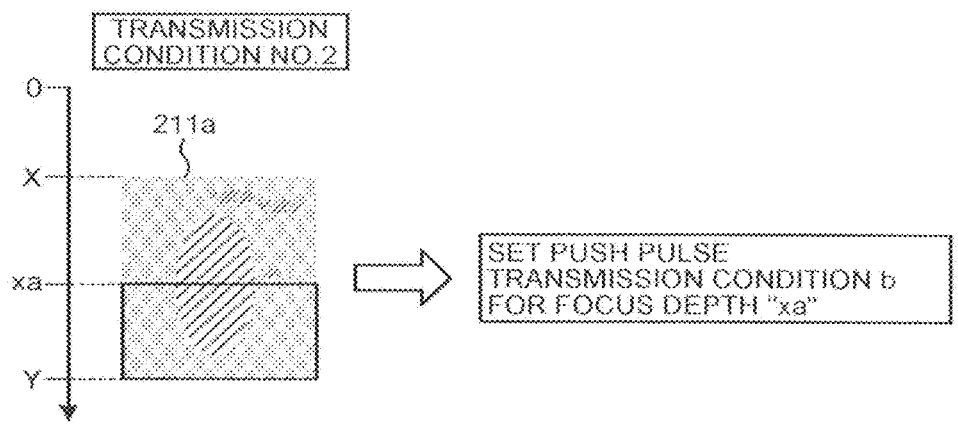
FIG. 18A, FIG. 18B, and FIG. 18C are diagrams for illustrating the second embodiment.
Figure 18B:
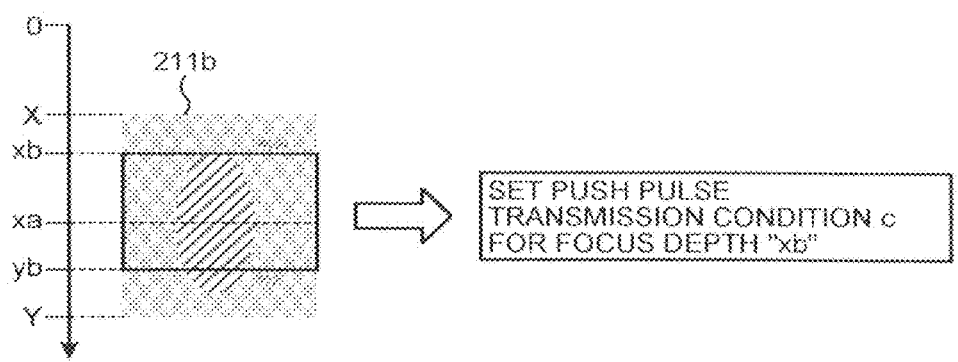
Figure 18C:
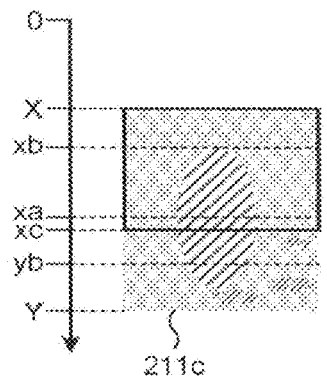

The first embodiment describes a case of searching for a plurality of kinds of push pulse transmission conditions for the ROI from the depth information table and setting them. A second embodiment describes a case of setting a plurality of kinds of push pulse transmission conditions for the ROI adaptively in accordance with a subject P to be imaged with reference to FIG. 18A, FIG. 18B, and FIG. 18C. FIG. 18A, FIG. 18B, and FIG. 18C are diagrams for describing the second embodiment.

An ultrasonic diagnostic apparatus according to the second embodiment is configured in the same manner as the ultrasonic diagnostic apparatus according to the first embodiment illustrated in FIG. 1, except that the setting unit 17 according to the second embodiment performs the following processing.

First, the setting unit 17 according to the second embodiment determines a low-reliability region in the hardness image data of the ROI corresponding to the push pulse transmitted on a given transmission condition. The hardness image data of the ROI is image data based on the hardness distribution information as an example of the distribution information based on the displacement information of the ROI. The setting unit 17 sets a transmission condition on which a shear wave speed is observed in living tissue in a partial region of the low-reliability region as a new given transmission condition. Specifically, the setting unit 17 determines a low-reliability region in the depth direction in image data (hardness image data, for example) on a given transmission condition. The setting unit 17 sets a transmission condition on which a shear wave speed is observed in living tissue in a partial region in the depth direction of the low-reliability region in the depth direction as the new given transmission condition.

The setting unit 17 repeats this processing, thereby setting a plurality of kinds of push pulse transmission conditions for the ROI. The setting unit 17 according to the second embodiment, for example, as illustrated in FIG. 18A, acquires the upper limit depth "X" and the lower limit depth "Y" of the ROI 40 set by the operator in the same manner as the first embodiment. The setting unit 17 refers to the depth information table and determines, as illustrated in FIG. 18A, the transmission condition of "transmission condition No. 2" to be the "first push pulse transmission condition" from the lower limit depth "Y". More simply, the push pulse condition with the lower limit depth "Y" of the ROI 40 set by the operator as the focus depth may be determined to be the "first push pulse transmission condition".

The second embodiment generates shear wave speed image data 211a corresponding to the "first push pulse transmission condition" set by the setting unit 17 by the processing of the transmitter 11, the receiver 12, the signal processing unit 13, and the image generating unit 14 (refer to FIG. 18A). In the shear wave speed image data 211a, the setting unit 17 determines the low-reliability region based on the variance or standard deviation of shear wave speed values in a local small region. Alternatively, the setting unit 17 determines the low-reliability region based on the magnitude of displacements at the respective points of the maximum displacement image data corresponding to the shear wave speed image data 211a.

The setting unit 17, for example, as illustrated in FIG. 18A, determines that the reliability is low in a region shallower than the focus depth "xa" and determines that the reliability is high in "xa to Y". The setting unit 17, for example, as illustrated in FIG. 18A, sets a push pulse transmission condition b for the focus depth "xa". The setting unit 17 sets a transmission aperture, a drive voltage, a transmission frequency, and a burst length to transmit the push pulse with the focus length "xa", thereby setting the push pulse transmission condition b. Because "X<xa" as illustrated in FIG. 18A, the setting unit 17 sets a divided ROI of "xa to Y" within the ROI 40. In the above example, the setting unit 17 searches for a transmission condition suitable for a region including the deepest part of the ROI 40 from the depth information table and determines a transmission condition suitable for the residual region from image analysis.

As illustrated in FIG. 18B, shear wave speed image data 211b corresponding to the "push pulse transmission condition b" set by the setting unit 17 is generated. The setting unit 17 analyzes the shear wave speed image data 211b, and as illustrated in FIG. 18B, determines that the reliability is low in the region shallower than the depth "xb" and that the reliability is low in the region deeper than the depth "yb". The setting unit 17 determines that the reliability is high in "xb to yb" of the shear wave speed image data 211b. The setting unit 17, for example, as illustrated in FIG. 18B, sets a push pulse transmission condition c for the focus depth "xb". Because "X<xb" as illustrated in FIG. 18B, the setting unit 17 sets a divided ROI of "xb to yb" within the ROI 40.

As illustrated in FIG. 18C, shear wave speed image data 211c corresponding to the "push pulse transmission condition c" set by the setting unit 17 is generated. The setting unit 17 analyzes the shear wave speed image data 211c, and as illustrated in FIG. 18C, determines that the reliability is low in the region deeper than the depth "xc". Because the reliability is high in "X to xc" in the shear wave speed image data 211c as illustrated in FIG. 18C, the setting unit 17 does not perform new setting of the transmission condition and sets a divided ROI of "X to xc" within the ROI 40. In other words, the setting unit 17 has set a plurality of divided ROIs that completely cover the ROI 40 and then ends the transmission condition setting processing.

The image generating unit 14 composes the shear wave speed image data 211a, the shear wave speed image data 211b, and the shear wave speed image data 211c based on the division patterns of "xa to Y", "xb to yb", and "X to xc" and outputs the composite image data as the shear wave speed image data of the ROI 40. For the image composition processing, the processing described in the first embodiment is used. The details described in the first embodiment can also be used in the second embodiment, except that a plurality of transmission conditions are set by the image analysis adaptively.

Figure 19:
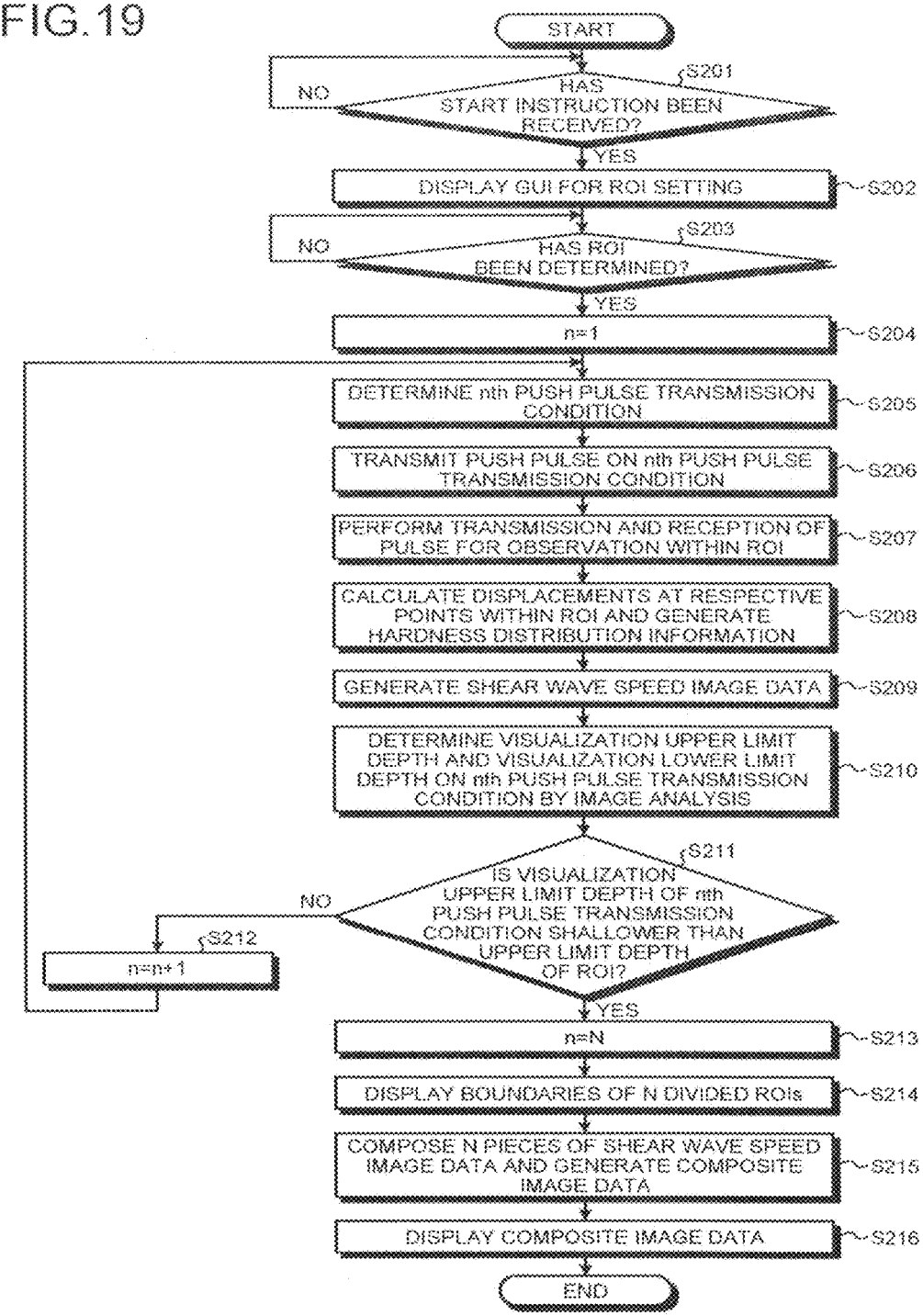
FIG. 19 is a flowchart for illustrating a processing example of an ultrasonic diagnostic apparatus according to the second embodiment.

Described next with reference to FIG. 19 is an example of the processing of the ultrasonic diagnostic apparatus according to the second embodiment. FIG. 19 is a flowchart for illustrating a processing example of the ultrasonic diagnostic apparatus according to the second embodiment.

As illustrated in FIG. 19, the controller 18 of the ultrasonic diagnostic apparatus according to the second embodiment determines whether a start instruction for starting the processing of the setting unit 17 has been received from the operator (Step S201). If the start instruction has not been received (No at Step S201), the controller 18 waits until the start instruction is received.

If the start instruction has been received (Yes at Step S201), the monitor 2 displays a GUI for ROI setting by the control of the controller 18 (Step S202). The controller 18 then determines whether the ROI has been set (Step S203). If the ROI has not been determined (No at Step S203), the controller 18 waits until the ROI is set. If the ROI has been set (Yes at Step S203), the setting unit 17 sets "n=1" (Step S204) and determines the nth push pulse transmission condition (Step S205). The second embodiment sets the first push pulse transmission condition in the same manner as the first embodiment.

By the control of the controller 18 that has received the notification of the setting unit 17, the transmitter 11 transmits the push pulse from the ultrasonic probe 1 on the nth push pulse transmission condition (Step S206). By the control of the transmitter 11 and the receiver 12, the ultrasonic probe 1 performs the transmission and reception of the pulse for observation within the ROI (Step S207), and the signal processing unit 13 calculates displacements at the respective points (respective sample points) within the ROI and generates the hardness distribution information (Step S208). The image generating unit 14 generates the shear wave speed image data on the nth push pulse transmission condition (Step S209).

The setting unit 17 determines the visualization upper limit depth and the visualization lower limit depth on the nth push pulse transmission condition by image analysis (Step S210). The setting unit 17 determines whether the visualization upper limit depth of the nth push pulse transmission condition is shallower than the upper limit depth of the ROI (Step S211). If the visualization upper limit depth of the nth push pulse transmission condition is deeper than the upper limit depth of the ROI (No at Step S211), the setting unit 17 increments "n" to "n=n+1" (Step S212), then returns to Step S205 to determine the nth push pulse transmission condition. For the second and later ones, the setting unit 17 determines adaptive push pulse transmission conditions.

If the visualization upper limit depth of the nth push pulse transmission condition is shallower than the upper limit depth of the ROI (Yes at Step S211), the setting unit 17 sets "n=N" (Step S213) and notifies the controller 18 of the fact that the N divided ROIs have been set.

By the control of the controller 18, the monitor 2 displays the boundaries of the N divided ROIs (Step S214). This processing is the same as the processing illustrated in FIG. 12A and FIG. 12B of the first embodiment.

By the instruction of the controller 18, the image generating unit 14 composes N pieces of shear wave speed image data to generate composite image data (Step S215). By the control of the controller 18, the monitor 2 displays the composite image data as the shear wave speed image data of the entire ROI (Step S216). This ends the photographing processing for the shear wave speed image data.

When the request input by the operator is a photographing request for video of the shear wave speed image data, the pieces of processing from Step S204 to Step S216 are repeated by the control of the controller 18 until a photographing end request is received. Alternatively, a plurality of kinds of transmission conditions and ROI division patterns set by the setting unit 17 in the first processing may be used continuously to generate and display the shear wave speed image data on a time-series basis.

As described above, the second embodiment sets a plurality of push pulse transmission conditions to give a push pulse that generates an ideal shear wave in accordance with the respective places within the ROI adaptively in accordance with the subject to be imaged. Thus, the second embodiment can surely obtain high-quality images indicating the hardness of living tissue.

Figure 20A:
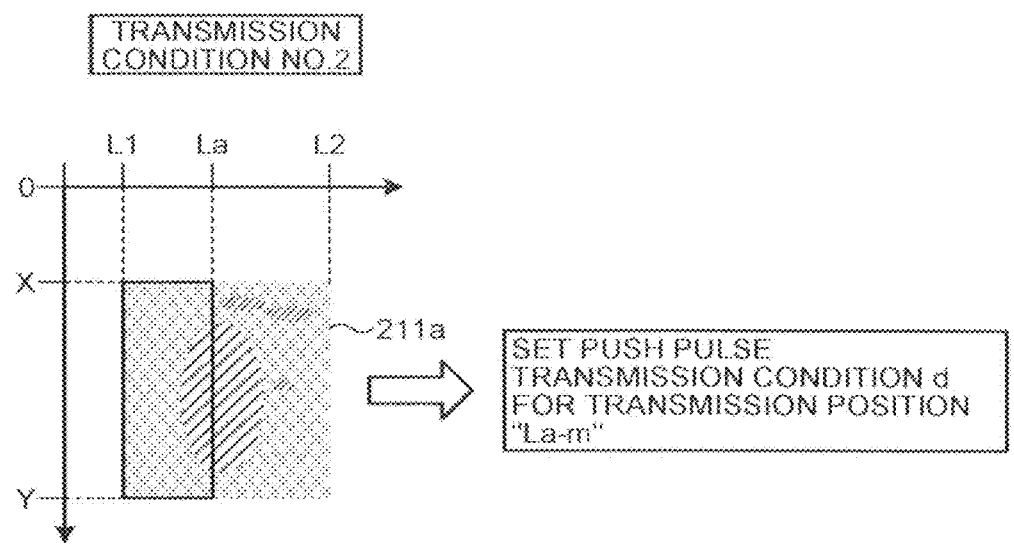
FIG. 20A and FIG. 20B are diagrams for illustrating the first modification of the second embodiment.
Figure 20B:
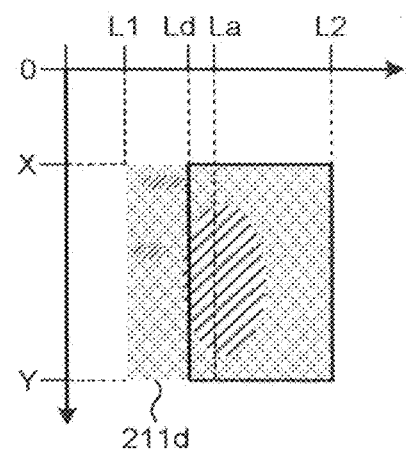

As described in the first embodiment, the lateral position of the push pulse transmission is changed by a preset value in accordance with the width of the ROI in the lateral direction in order to improve the observation sensitivity of the shear wave speed. However, in order to surely improve the observation sensitivity of the shear wave speed, it is desirable that the lateral position of the push pulse transmission be changed in accordance with a site to be photographed adaptively. In other words, it is desirable that the ROI be divided in the lateral direction adaptively. FIG. 20A and FIG. 20B are diagrams for illustrating a first modification of the second embodiment.

The setting unit 17 according to the first modification of the second embodiment determines a low-reliability region in the lateral direction in hardness image data on a given transmission condition and newly sets a transmission condition on which a shear wave speed is observed in living tissue in a partial region in the lateral direction of the determined region. The hardness image data is image data based on the hardness distribution information as an example of the distribution information based on the displacement information.

The setting unit 17, for example, as illustrated in FIG. 20A, acquires the upper limit depth "X" and the lower limit depth "Y" and the left end "L1" and the right end "L2" in the lateral direction of the ROI 40 set by the operator. The setting unit 17 refers to the depth information table, and as illustrated in FIG. 20A, determines the transmission condition of "transmission condition No. 2" to be the "first push pulse transmission condition" from the lower limit depth "Y".

The setting unit 17, as illustrated in FIG. 20A, determines in the shear wave speed image data 211a corresponding to the "first push pulse transmission condition" that the reliability is low in the lateral direction "La to L2" and that the reliability is high in "L1 to La". The setting unit 17, for example, as illustrated in FIG. 20A, sets a push pulse transmission condition d for the lateral position of transmission "La−m". A preset value is, for example, used for "m". Because "L2>La" as illustrated in FIG. 20A, the setting unit 17 sets a divided ROI of "L1 to La" within the ROI 40.

As illustrated in FIG. 20B, shear wave speed image data 211d corresponding to the "push pulse transmission condition d" set by the setting unit 17 is generated. The setting unit 17 analyzes the shear wave speed image data 211d, and as illustrated in FIG. 20B, determines that the reliability is low in the lateral direction "L1 to Ld". Because the reliability is high in "Ld to L" in the shear wave speed image data 211d as illustrated in FIG. 20B, the setting unit 17 does not perform new setting of the transmission condition and sets a divided ROI of "Ld to L" within the ROI 40. In other words, the setting unit 17 has set a plurality of divided ROIs that completely cover the ROI 40 and then ends the transmission condition setting processing.

The image generating unit 14 composes the shear wave speed image data 211a and the shear wave speed image data 211d based on the division patterns of "L1 to La" and "Ld to L" and outputs the composite image data as the shear wave speed image data of the ROI 40.

Figure 21A:
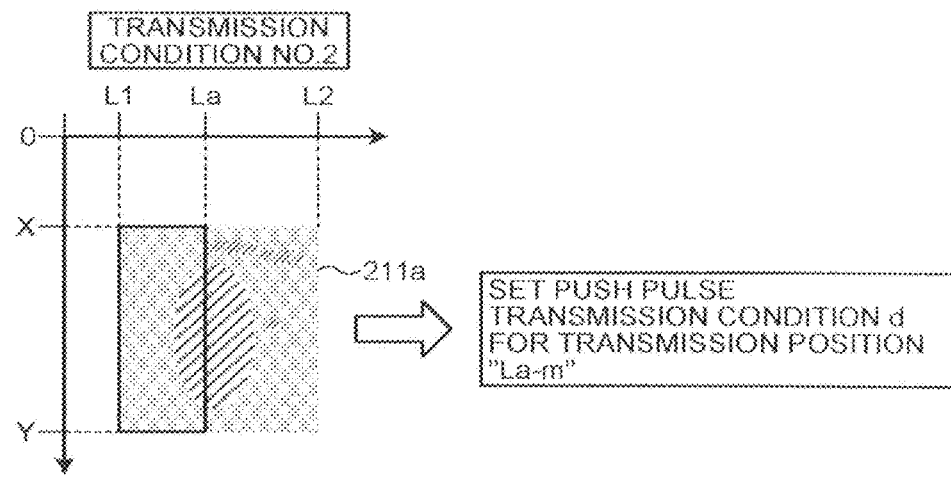
FIG. 21A, FIG. 21B, and FIG. 21C are diagrams for illustrating the second modification of the second embodiment.
Figure 21B:
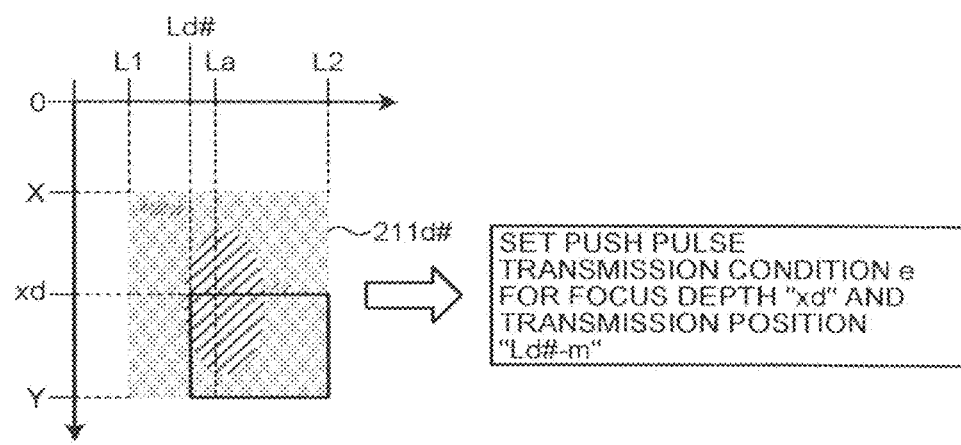
Figure 21C:
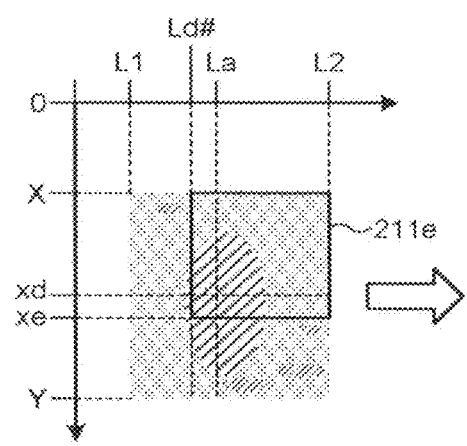

In order to further surely improve the observation sensitivity of the shear wave speed, it is desirable to divide the ROI adaptively in both the depth direction and the lateral direction. FIG. 21A, FIG. 21B, and FIG. 21C are diagrams for illustrating a second modification of the second embodiment.

The processing performed by the setting unit 17 in FIG. 21A is the same as the processing described with reference to FIG. 20A. In other words, the setting unit 17, as illustrated in FIG. 21A, determines the transmission condition of "transmission condition No. 2" to be the "first push pulse transmission condition" from the lower limit depth "Y" of the ROI 40. The setting unit 17, as illustrated in FIG. 21A, determines in the shear wave speed image data 211a that the reliability is high in "L1 to La". The setting unit 17, as illustrated in FIG. 21A, sets the push pulse transmission condition d for the lateral position of transmission "La−m". Because "L2>La" as illustrated in FIG. 21A, the setting unit 17 sets a divided ROI of "L1 to La" within the ROI 40.

As illustrated in FIG. 21B, shear wave speed image data 211d# corresponding to the "push pulse transmission condition d" set by the setting unit 17 is generated. The setting unit 17 analyzes the shear wave speed image data 211d#, and as illustrated in FIG. 21B, determines that the reliability is high in the region of "lateral direction: Ld# to L2, depth direction: xd to Y". The setting unit 17, as illustrated in FIG. 21B, sets a push pulse transmission condition e for the focus depth "xd" and the lateral position of transmission "Ld#-m". Because "xd>X" as illustrated in FIG. 21B, the setting unit 17 sets a divided ROI of "lateral direction: Ld# to L2, depth direction: xd to Y" within the ROI 40.

As illustrated in FIG. 21C, shear wave speed image data 211e corresponding to the "push pulse transmission condition e" set by the setting unit 17 is generated. The setting unit 17 analyzes the shear wave speed image data 211e, and as illustrated in FIG. 21C, determines that the reliability is high in the region of "lateral direction: Ld# to L2, depth direction: xe to X" and sets this region as a divided ROI. The setting unit 17 has set a plurality of divided ROIs that completely cover the ROI 40 and then ends the transmission condition setting processing.

The image generating unit 14 composes the shear wave speed image data 211a, the shear wave speed image data 211d#, and the shear wave speed image data 211e based on the division patterns of "L1 to La", "lateral direction: Ld# to L2, depth direction: xd to Y", and "lateral direction: Ld# to L2, depth direction: xe to X" and outputs the composite image data as the shear wave speed image data of the ROI 40.

Performing the first modification and the second modification can also surely obtain high-quality images indicating the hardness of living tissue.

Third Embodiment

Figure 22:
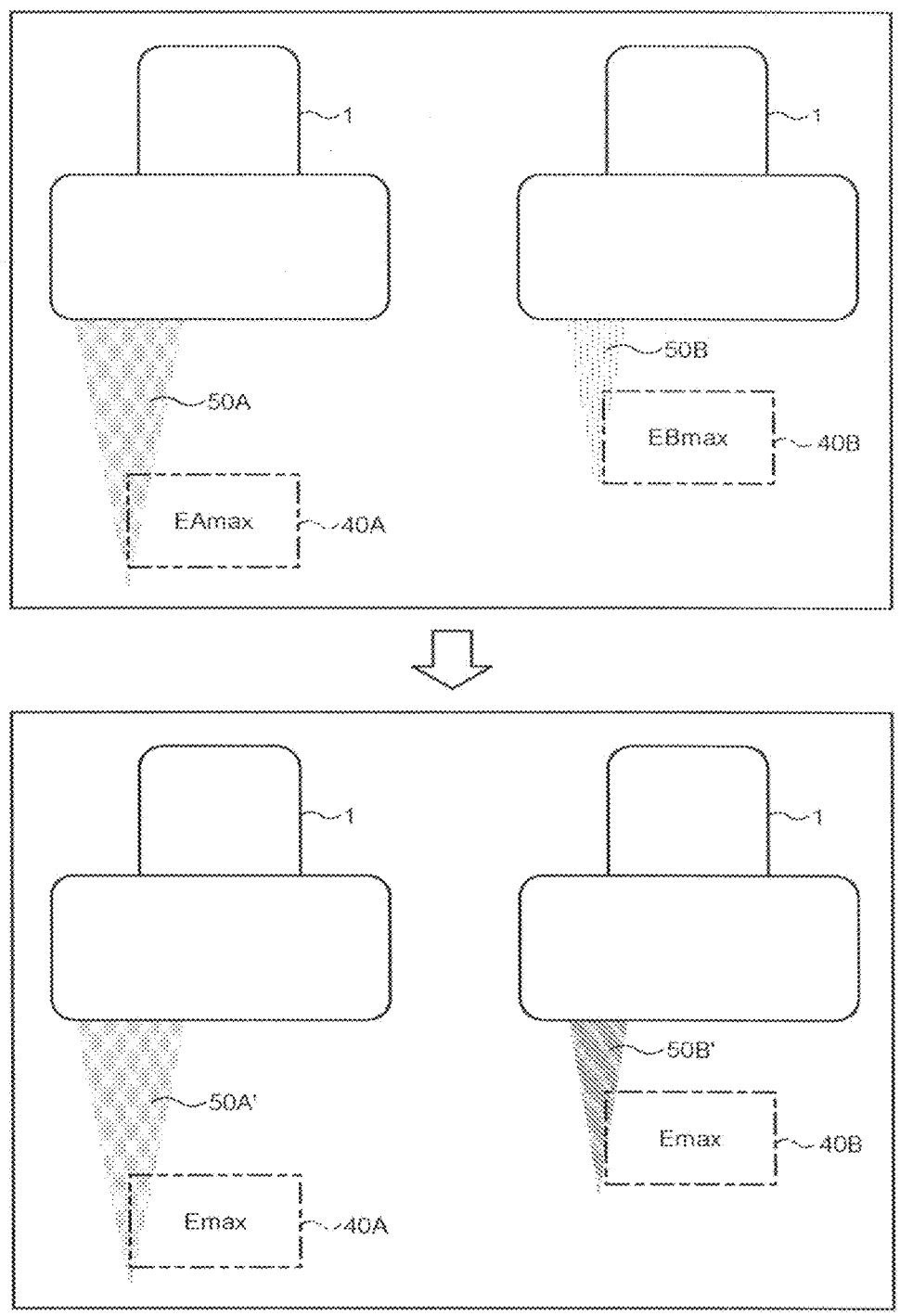
FIG. 22, FIG. 23A, and FIG. 23B are diagrams for illustrating the third embodiment.
Figures 23A, 23B:
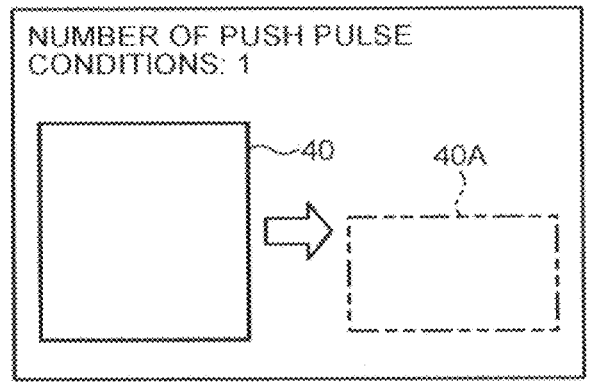

A third embodiment describes a modification applicable when performing the processing described in the first embodiment and the second embodiment with reference to FIG. 22, FIG. 23A, and FIG. 23B. FIG. 22, FIG. 23A, and FIG. 23B are diagrams illustrating the third embodiment.

The setting unit 17 according to the third embodiment sets a plurality of transmission conditions so that pieces of arrival power or arrival energy when the push pulses transmitted from the ultrasonic probe 1 arrive at respective divided ROIs will be substantially the same. The setting unit 17, for example, as illustrated in the upper diagram of FIG. 22, calculates an estimated value of the maximum energy "EAmax" when the push pulse 50A transmitted on the "first push pulse transmission condition" arrives at the divided ROI 40A. Similarly, the setting unit 17, for example, as illustrated in the upper diagram of FIG. 22, calculates an estimated value of the maximum energy "EBmax" when the push pulse 50B transmitted on the "second push pulse transmission condition" arrives at the divided ROI 40B.

The setting unit 17, as illustrated in the lower diagram of FIG. 22, adjusts the burst length or sound pressure of the "first push pulse transmission condition" so that a push pulse 50A' that changes "EAmax" into "Emax" will be transmitted. The setting unit 17, as illustrated in the lower diagram of FIG. 22, adjusts the burst length or sound pressure of the "second push pulse transmission condition" so that a push pulse 50B' that changes "EBmax" into "Emax" will be transmitted.

Performing the above processing can reduce, for example, the burst length or sound pressure of the push pulse for a shallow region in particular and can prevent the ultrasonic probe 1 from producing unnecessary heat while maintaining required observation accuracy of the shear wave speed.

In order to simplify the processing of the setting unit 17, the third embodiment may divide the ROI set by the operator with the number of division determined in advance in accordance with the width of the ROI in the depth direction or the width of division determined in advance in accordance with the width of the ROI in the depth direction. In FIG. 23A, for example, when the width of the ROI in the depth direction (WD) is "WD≤WD1", the "number of division: 1" is set; when "WD1<WD≤WD2", the "number of division: 2" is set; when "WD2<WD≤WD3", the "number of division: 3" is set; and when "WD3<WD≤WD4", the "number of division: 4" is set.

When the width of the ROI 40 in the depth direction "WD=Y−X" is "WD2<WD≤WD3", for example, the setting unit 17 equally divides the ROI 40 into three stages and sets three kinds of push pulse transmission conditions. The setting unit 17 according to the first embodiment, for example, acquires a transmission condition of a focus depth closest to the center depth position of each stage from the table. The setting unit 17 according to the second embodiment, for example, calculates a transmission condition focused on the center depth position of each stage.

Alternatively, the setting unit 17 may set a value obtained by rounding a value obtained by dividing the width of the ROI 40 in the depth direction "WD=Y−X" by the width of division "wD" set in advance to be the number of division. Alternatively, different values may be set for the width of division in accordance with the value of WD.

The setting unit 17 according to the third embodiment may adjust the ROI set by the operator within the range having the upper limit value of the number of times of transmission of the push pulse or of the number of transmission conditions of the push pulse. In other words, the number of times of transmission of the push pulse is determined by the number of transmission conditions, the width in the lateral direction, and the number of parallel simultaneous reception. A larger number of times of transmission of the push pulse results in a lower frame rate and causes the ultrasonic probe 1 to produce heat.

This modification sets the upper limit value of the number of times of transmission of the push pulse or of the number of transmission conditions of the push pulse in advance. The setting unit 17 places limitations so that the ROI that will require the number of times of the push pulse exceeding the upper limit cannot be set.

As illustrated in FIG. 23B, for example, it is assumed that the "number of push pulse conditions: 1" is set in advance. The setting unit 17 determines that when the ROI 40 is divided into the divided ROI 40A and the divided ROI 40B, the number of push pulse conditions is "2", which exceeds the upper limit "1". In such a case, the setting unit 17, for example, as illustrated in FIG. 23B, changes the ROI 40 into the divided ROI 40A and uses only the push pulse transmission condition corresponding to the divided ROI 40A to perform elastography.

Alternatively, it is assumed that the number of times of transmission of the push pulse is set to be "4". It is assumed that three times of the push pulse transmission on the "first push pulse transmission condition" is required and that three times of the push pulse transmission on the "second push pulse transmission condition" is required within the ROI 40. In such a case, the setting unit 17 reduces the ROI 40 by "⅔" in the lateral direction so that the number of times of transmission of the push pulse will be "4". In such a case, the divided ROI 40A and the divided ROI 40B are separately reduced by "⅔" in the lateral direction.

Placing limitations using the upper limit can reduce the occurrence of artifacts.

The respective components of the respective apparatuses illustrated in the description of the first to the third embodiments are functionally conceptual and are not necessarily configured physically as illustrated. In other words, the specific forms of the distribution and integration of the respective apparatuses are not limited to the illustrated ones, and the whole or part thereof may be configured through functional or physical distribution and integration on any desirable unit in accordance with various kinds of loads and use conditions, for example. The whole or part of the processing functions performed by the respective apparatuses can be performed by a CPU and a computer program executed by the CPU or performed by hardware by wired logic.

The method of ultrasonic imaging described in the first to the third embodiments can be performed by executing an ultrasonic imaging program prepared in advance by computers such as personal computers and workstations. This ultrasonic imaging program may be distributed via a network such as the Internet. This ultrasonic imaging program can be stored in a computer-readable, non-transitory recording medium such as a hard disk, a flexible disk (FD), a CD-ROM, an MO, and a DVD and can be read and executed from the non-transitory recording medium by a computer.

As described above, the first to the third embodiments can obtain high-quality images indicating the hardness of living tissue.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
   a storage configured to store therein, for each of a plurality of transmission conditions of a pushing pulse including a focus depth, depth information indicating an upper limit depth and a lower limit depth of a region of interest (ROI), and
   processing circuitry configured to
      set a region for observation according to an instruction from an operator through an input device,
      compare the depth information and range of depth of the region for observation set according to the instruction from the operator,
      set, based on a result of the comparison, a plurality of ROIs comprising a first ROI and a second ROI, the second ROI being adjacent to the first ROI in a depth direction corresponding to a transmitting direction of an ultrasonic probe or partly overlapping with the first ROI in the depth direction, such that the region for observation is covered by the ROIs,
      cause the ultrasonic probe to transmit a first pushing pulse focused at a first focus depth included in a transmission condition corresponding to the first ROI, the first pushing pulse causing a displacement in the first ROI,
      cause the ultrasonic probe to transmit and receive a first observing pulse shortly after transmission of the first pushing pulse for observing the displacement in the first ROI,
      cause the ultrasonic probe to transmit a second pushing pulse focused at a second focus depth included in a transmission condition corresponding to the second ROI after transmission and reception of the first observing pulse, the second pushing pulse causing a displacement in the second ROI, the first focus depth and the second focus depth being different from each other,
      cause the ultrasonic probe to transmit and receive a second observing pulse shortly after transmission of the second pushing pulse for observing the displacement in the second ROI,
      generate first displacement information by analyzing the received first observing pulse for each sampling position in the first ROI,
      generate a first image of the first ROI based on the first displacement information,
      generate second displacement information by analyzing the received second observing pulse for each sampling position in the second ROI,
      generate a second image of the second ROI based on the second displacement information, and
      generate a composite image based on the first image and the second image.

2. The ultrasonic diagnostic apparatus according to claim 1, wherein the processing circuitry is configured to determine a low-reliability region in image data based on the displacement information of the region of interest corresponding to the pushing pulse transmitted on a given transmission condition and repeats processing that sets a transmission condition on which a shear wave speed is observed in living tissue in a partial region of the determined region as a new given transmission condition, thereby setting the first focus depth and the second focus depth.

3. The ultrasonic diagnostic apparatus according to claim 2, wherein the processing circuitry is configured to determine a low-reliability region in the depth direction in image data based on the displacement information on the given transmission condition and sets a transmission condition on which a shear wave speed is observed in living tissue in a partial region in the depth direction of the determined region in the depth direction as a new given transmission condition.

4. The ultrasonic diagnostic apparatus according to claim 2, wherein the processing circuitry is configured to determine a low-reliability region in a lateral direction in image data based on the displacement information of the given transmission condition and sets a transmission condition on which a shear wave speed is observed in living tissue in a partial region in the lateral direction of the determined region in the lateral direction as a new transmission condition.

5. The ultrasonic diagnostic apparatus according to claim 1, wherein
   the processing circuitry is configured to display the first ROI and the second ROI on a display.

6. The ultrasonic diagnostic apparatus according to claim 1, wherein the transmission conditions differ from each other in at least one of a focus depth, a transmission aperture, a transmission frequency, and a burst length of the pushing pulse.

7. The ultrasonic diagnostic apparatus according to claim 1, wherein the processing circuitry is configured to set transmission conditions so that pieces of arrival power or arrival energy when the pushing pulse transmitted from the ultrasonic probe arrive at the respective regions of interest are substantially the same.

8. The ultrasonic diagnostic apparatus according to claim 1, wherein the processing circuitry is configured to adjust the region of interest within the range having an upper limit value of the number of times of transmission of the pushing pulse or the number of transmission conditions of the pushing pulse.

9. The ultrasonic diagnostic apparatus according to claim 1, wherein the storage is configured to store the depth information in a table, the depth information acquired in advance as a result of a preliminary test using a phantom, the depth information further indicating an aperture width, a focus depth, a drive voltage, frequency, and a burst length of the pushing pulse.

10. The ultrasonic diagnostic apparatus according to claim 1, wherein the processing circuitry is configured to
 display the first ROI and the second ROI on a display along with a graphical indicator indicating a boundary of the first ROI or the second ROI,
 receive, after displaying the first ROI and the second ROI and after setting of the plurality of ROIs has been approved, an imaging start request,
 cause, after receiving the imaging start request and after displaying the first ROI and the second ROI, the ultrasonic probe to transmit the first pushing pulse focused at the first focus depth included in the transmission condition corresponding to the first ROI, and
 cause, after receiving the imaging start request and after displaying the first ROI and the second ROI, the ultrasonic probe to transmit and receive the first observing pulse shortly after transmission of the first pushing pulse for observing the displacement in the first ROI.

11. A method of ultrasonic imaging comprising:
 setting a region for observation according to instructions from an operator through an input device;
 comparing depth information and range of depth of the region for observation set according to the instruction from the operator;
 setting, based on a result of the comparison, a plurality of regions of interest (ROIs) comprising a first ROI and a second ROI, the second ROI being adjacent to the first ROI in a depth direction corresponding to a transmitting direction of an ultrasonic probe or partly overlapping with the first ROI in the depth direction, the depth information indicating an upper limit depth and a lower limit depth of each ROI corresponding to one of a plurality of transmission conditions of pushing pulse including a focus depth, such that the region for observation is covered by the ROIs;
 causing the ultrasonic probe to transmit a first pushing pulse focused at a first focus depth included in a transmission condition corresponding the first ROI, the first pushing pulse causing a displacement in the first ROI;
 causing the ultrasonic probe to transmit and receive a first observing pulse shortly after transmission of the first pushing pulse for observing the displacement in the first ROI;
 causing the ultrasonic probe to transmit a second pushing pulse focused at a second focus depth included in a transmission condition corresponding to the second ROI after transmission and reception of the first observing pulse, the second pushing pulse causing a displacement in the second ROI, the first focus depth and the second focus depth being different from each other;
 causing the ultrasonic probe to transmit and receive a second observing pulse shortly after transmission of the second pushing pulse for observing the displacement in the second ROI;
 generating first displacement information by analyzing the received first observing pulse for each sampling position in the first ROI;
 generating a first image of the first ROI based on the first displacement information;
 generating second displacement information by analyzing the received second observing pulse for each sampling position in the second ROI;
 generating a second image of the second ROI based on the second displacement information; and
 generating a composite image based on the first image and the second image.

* * * * *